(12) United States Patent
Hammock et al.

(10) Patent No.: US 7,951,831 B2
(45) Date of Patent: May 31, 2011

(54) USE OF INHIBITORS OF SOLUBLE EPOXIDE HYDROLASE TO SYNERGIZE ACTIVITY OF COX AND 5-LOX INHIBITORS

(75) Inventors: Bruce D. Hammock, Davis, CA (US); Kara Schmelzer, Davis, CA (US); Ahmet Bora Inceoglu, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/330,033

(22) Filed: Jan. 10, 2006

(65) Prior Publication Data

US 2006/0178347 A1 Aug. 10, 2006

Related U.S. Application Data

(60) Provisional application No. 60/643,028, filed on Jan. 10, 2005.

(51) Int. Cl.
*A01N 43/56* (2006.01)
*A61K 31/18* (2006.01)

(52) U.S. Cl. .................................... 514/406; 514/601
(58) Field of Classification Search .................. 514/406, 514/601
See application file for complete search history.

(56) References Cited

U.S. PATENT DOCUMENTS

| 5,962,455 A | 10/1999 | Blum et al. |
|---|---|---|
| 6,136,839 A | 10/2000 | Isakson et al. |
| 6,531,506 B1 | 3/2003 | Kroetz et al. |
| 2005/0026844 A1 | 2/2005 | Hammock et al. |

FOREIGN PATENT DOCUMENTS

| JP | 5 059032 A | 3/1993 |
|---|---|---|
| WO | 99/54282 A1 | 10/1999 |
| WO | 01/10438 A1 | 2/2001 |
| WO | 02/089787 A1 | 11/2002 |
| WO | 2004/089296 A2 | 10/2004 |
| WO | 2005/089380 A2 | 9/2005 |

OTHER PUBLICATIONS

Chiang, N., et al., "Aspirin triggers anti-inflammatory 15-epi-lipoxin $A_4$ and inhibits thromboxane in a randomized human trial," *PNAS* vol. 101(42), pp. 15178-15183 (Oct. 19, 2004).
Finley, B., et al., "Increased cholesterol epoxide hydrolase activity in clofibrate-fed animals," *Biochemical Pharmacology*, vol. 37(16), pp. 3169-3175 (1988).
Gilroy, D., et al., "COX-2 expression and cell cycle progression in human fibroblasts," *Am. J. Physiol. Cell Physiol.*, vol. 281, pp. C188-C194 (2001).
Gilroy, D., et al., "Cell cycle-dependent expression of cyclooxygenase-2 in human fibroblasts," *The FASEB Journal*, vol. 15, pp. 288-290 (Feb. 2001).
Karara, A., et al., "Endogenous epoxyeicosatrienoic acids," *The Journal of Biological Chemistry*, vol. 264 (33), pp. 19822-19827 (1989).
Meade, E., et al., "Peroxisome proliferators enhance cyclooxygenase-2 expression in epithelial cells," *The Journal of Biological Chemistry*, vol. 274(12), pp. 8328-8334 (1999).
Seibert, K., et al., "Role of inducible cyclooxygenase (COX-2_in inflammation," Receptor, vol. 4, pp. 17-23 (1994).
Serhan, C., et al., "Unorthodox routes to prostandoid formation: new twists in cyclooxygenase-initiated pathways," *The Journal of Clinical Investigation*, vol. 107(12), pp. 1481-1489 (Jun. 2001).
Goodman & Gilman's: "The Pharmacological Basis of Therapeutics"; 2001, Tenth Edition, Table 27-3, p. 710.
Office Communication from U.S. Appl. No. 10/694,641, dated Jun. 22, 2010 (7 pages).
Extended Supplementary European Search Report and Written Opinion mailed Sep. 27, 2010, from Application No. 06733676.8.

*Primary Examiner* — Sreeni Padmanabhan
*Assistant Examiner* — Renee Claytor
(74) *Attorney, Agent, or Firm* — Weaver Austin Villeneuve & Sampson LLP

(57) ABSTRACT

The invention relates to methods, compositions, and uses of those compositions for making medicaments, for potentiating the beneficial effects of inhibitors of COX-1, COX-2, and 5-LOX, and reducing adverse effects, by also administering inhibitors of soluble epoxide hydrolase ("sEH"), with or without also administering one or more cis-epoxyeicosantrienoic acids. The invention further relates to the use of inhibitors of sEH as analgesics and to methods and compositions of epoxides of eicosapentaenoic acid and docosahexaenoic acid, optionally with an inhibitor of sEH, to reduce pain or inflammation or both.

13 Claims, 8 Drawing Sheets

Fig 2: P450 metabolites of arachidonic acid epoxides (A) and diols (B)
Bar correspond to mean concentration ± stdev (n=4) of mice exposed to saline (control (■)) or LPS (■)

SEQUENCE LISTING

<160> NUMBER OF SEQ ID NOS: 38

<210> SEQ ID NO 1

<400> SEQUENCE: 1

000

```
<210> SEQ ID NO 2
<400> SEQUENCE: 2

000

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:soluble
      epoxide hydrolase (sEH) target sequence 1

<400> SEQUENCE: 3
cagtgttcat tggccatgac tgg                                              23

<210> SEQ ID NO 4
<211> LENGTH: 21
<212> TYPE: DNA
<213> ORGANISM: Artificial Sequence
<220> FEATURE:
<223> OTHER INFORMATION: Description of Combined DNA/RNA Molecule:
      soluble epoxide hydrolase (sEH) sense short or small
      interfering RNA (siRNA) for target sequence 1
<220> FEATURE:
<223> OTHER INFORMATION: Description of Artificial Sequence:soluble
      epoxide hydrolase (sEH) sense short or small interfering
      RNA (siRNA) for target sequence 1

<400> SEQUENCE: 4
guguucauug gccaugacut t                                                21

<210> SEQ ID NO 5
<211> LENGTH: 21
<212> TYPE: DNA
<213> ORGANISM: Artificial Sequence
<220> FEATURE:
<223> OTHER INFORMATION: Description of Combined DNA/RNA Molecule:
      soluble epoxide hydrolase (sEH) antisense short or small
      interfering RNA (siRNA) for target sequence 1
<220> FEATURE:
<223> OTHER INFORMATION: Description of Artificial Sequence:soluble
      epoxide hydrolase (sEH) antisense short or small interfering
      RNA (siRNA) for target sequence 1

<400> SEQUENCE: 5
agucauggcc aaugaacact t                                                21

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence:soluble
      epoxide hydrolase (sEH) target sequence 2

<400> SEQUENCE: 6
gaaaggctat ggagagtcat ctg                                              23

<210> SEQ ID NO 7
<211> LENGTH: 21
<212> TYPE: DNA
<213> ORGANISM: Artificial Sequence
<220> FEATURE:
<223> OTHER INFORMATION: Description of Combined DNA/RNA Molecule:
      soluble epoxide hydrolase (sEH) sense short or small
      interfering RNA (siRNA) for target sequence 2
<220> FEATURE:
<223> OTHER INFORMATION: Description of Artificial Sequence:soluble
      epoxide hydrolase (sEH) sense short or small interfering
```

RNA (siRNA) for target sequence 2

<400> SEQUENCE: 7
aaggcuaugg agagucauct t                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Combined DNA/RNA Molecule:
      soluble epoxide hydrolase (sEH) antisense short or small
      interfering RNA (siRNA) for target sequence 2
<220> FEATURE:
<223> OTHER INFORMATION: Description of Artificial Sequence:soluble
      epoxide hydrolase (sEH) antisense short or small
      interfering RNA (siRNA) for target sequence 2

<400> SEQUENCE: 8
gaugacucuc cauagccuut t                                              21

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:soluble
      epoxide hydrolase (sEH) target sequence 3

<400> SEQUENCE: 9
aaaggctatg gagagtcatc tgc                                            23

<210> SEQ ID NO 10
<211> LENGTH: 21
<212> TYPE: DNA
<213> ORGANISM: Artificial Sequence
<220> FEATURE:
<223> OTHER INFORMATION: Description of Combined DNA/RNA Molecule:
      soluble epoxide hydrolase (sEH) sense short or small
      interfering RNA (siRNA) for target sequence 3
<220> FEATURE:
<223> OTHER INFORMATION: Description of Artificial Sequence:soluble
      epoxide hydrolase (sEH) sense short or small interfering
      RNA (siRNA) for target sequence 3

<400> SEQUENCE: 10
aggcuaugga gagucaucut t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Combined DNA/RNA Molecule:
      soluble epoxide hydrolase (sEH) antisense short or small
      interfering RNA (siRNA) for target sequence 3
<220> FEATURE:
<223> OTHER INFORMATION: Description of Artificial Sequence:soluble
      epoxide hydrolase (sEH) antisense short or small
      interfering RNA (siRNA)

<400> SEQUENCE: 11
agaugacucu ccauagccut t                                              21

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence:soluble -continued epoxide hydrolase (sEH) target sequence 4

<400> SEQUENCE: 12
caagcagtgt tcattggcca tga                                            23

<210> SEQ ID NO 13
<211> LENGTH: 21
<212> TYPE: DNA
<213> ORGANISM: Artificial Sequence
<220> FEATURE:
<223> OTHER INFORMATION: Description of Combined DNA/RNA Molecule:
      soluble epoxide hydrolase (sEH) sense short or small
      interfering RNA (siRNA) for target sequence 4
<220> FEATURE:
<223> OTHER INFORMATION: Description of Artificial Sequence:soluble
      epoxide hydrolase (sEH) sense short or small interfering
      RNA (siRNA) for target sequence 4

<400> SEQUENCE: 13
agcaguguuc auuggccaut t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Combined DNA/RNA Molecule:
      soluble epoxide hydrolase (sEH) antisense short or small
      interfering RNA (siRNA) for target sequence 4
<220> FEATURE:
<223> OTHER INFORMATION: Description of Artificial Sequence:soluble
      epoxide hydrolase (sEH) antisense short or small
      interfering RNA (siRNA) for target sequence 4

<400> SEQUENCE: 14
auggccaaug aacacugcut t                                              21

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence:soluble
      epoxide hydrolase (sEH) target sequence 5

<400> SEQUENCE: 15
cagcacatgg aggactggat tcc                                            23

<210> SEQ ID NO 16
<211> LENGTH: 21
<212> TYPE: DNA
<213> ORGANISM: Artificial Sequence
<220> FEATURE:
<223> OTHER INFORMATION: Description of Combined DNA/RNA Molecule:
      soluble epoxide hydrolase (sEH) sense short or small
      interfering RNA (siRNA) for target sequence 5
<220> FEATURE:
<223> OTHER INFORMATION: Description of Artificial Sequence:soluble
      epoxide hydrolase (sEH) sense short or small interfering
      RNA (siRNA) for target sequence 5

<400> SEQUENCE: 16
gcacauggag gacuggauut t                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Combined DNA/RNA Molecule:

soluble epoxide hydrolase (sEH) antisense short or small
interfering RNA (siRNA) for target sequence 5
<220> FEATURE:
<223> OTHER INFORMATION: Description of Artificial Sequence:soluble
epoxide hydrolase (sEH) antisense short or small
interfering RNA (siRNA) for target sequence 5

<400> SEQUENCE: 17
aauccagucc uccaugugct t                                        21

<210> SEQ ID NO 18
<211> LENGTH: 9
<212> TYPE: DNA
<213> ORGANISM: Artificial Sequence
<220> FEATURE:
<223> OTHER INFORMATION: Description of Artificial Sequence:nine-
nucleotide spacer

<400> SEQUENCE: 18 ttcaagaga                                                       9

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence:soluble
epoxide hydrolase (sEH) target 1 for hairpin short or
small interfering RNA (siRNA)

<400> SEQUENCE: 19
cagtgttcat tggccatgac tgg                                      23

<210> SEQ ID NO 20
<211> LENGTH: 59
<212> TYPE: DNA
<213> ORGANISM: Artificial Sequence
<220> FEATURE:
<223> OTHER INFORMATION: Description of Artificial Sequence:soluble
epoxide hydrolase (sEH) sense strand of hairpin short or
small interfering RNA (siRNA) for target sequence 1

<400> SEQUENCE: 20
gatccccgtg ttcattggcc atgactttca agagaagtca tggccaatga acactttt     59

<210> SEQ ID NO 21
<211> LENGTH: 59
<212> TYPE: DNA
<213> ORGANISM: Artificial Sequence
<220> FEATURE:
<223> OTHER INFORMATION: Description of Artificial Sequence:soluble
epoxide hydrolase (sEH) antisense strand of hairpin short or
small interfering RNA (siRNA) for target sequence 1

<400> SEQUENCE: 21
agctaaaaag tgttcattgg ccatgacttc tcttgaaagt catggccaat gaacacggg     59

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence:soluble
epoxide hydrolase (sEH) target 2 for hairpin short or
small interfering RNA (siRNA)

<400> SEQUENCE: 22
gaaaggctat ggagagtcat ctg                                      23

<210> SEQ ID NO 23
<211> LENGTH: 59
<212> TYPE: DNA
<213> ORGANISM: Artificial Sequence
<220> FEATURE:
<223> OTHER INFORMATION: Description of Artificial Sequence:soluble
      epoxide hydrolase (sEH) sense strand of hairpin short or
      small interfering RNA (siRNA) for target sequence 2

<400> SEQUENCE: 23
gatccccaag gctatggaga gtcatcttca agagagatga ctctccatag ccttttttt      59

<210> SEQ ID NO 24
<211> LENGTH: 59
<212> TYPE: DNA
<213> ORGANISM: Artificial Sequence
<220> FEATURE:
<223> OTHER INFORMATION: Description of Artificial Sequence:soluble
      epoxide hydrolase (sEH) antisense strand of hairpin short or
      small interfering RNA (siRNA) for target sequence 2

<400> SEQUENCE: 24
agctaaaaaa aggctatgga gagtcatctc tcttgaagat gactctccat agccttggg      59

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence:soluble
      epoxide hydrolase (sEH) target 3 for hairpin short or
      small interfering RNA (siRNA)

<400> SEQUENCE: 25
aaaggctatg gagagtcatc tgc                                             23

<210> SEQ ID NO 26
<211> LENGTH: 59
<212> TYPE: DNA
<213> ORGANISM: Artificial Sequence
<220> FEATURE:
<223> OTHER INFORMATION: Description of Artificial Sequence:soluble
      epoxide hydrolase (sEH) sense strand of hairpin short or
      small interfering RNA (siRNA) for target sequence 3

<400> SEQUENCE: 26
gatccccagg ctatggagag tcatctttca agagaagatg actctccata gccttttt       59

<210> SEQ ID NO 27
<211> LENGTH: 59
<212> TYPE: DNA
<213> ORGANISM: Artificial Sequence
<220> FEATURE:
<223> OTHER INFORMATION: Description of Artificial Sequence:soluble
      epoxide hydrolase (sEH) antisense strand of hairpin short or
      small interfering RNA (siRNA) for target sequence 3

<400> SEQUENCE: 27
agctaaaaaa ggctatggag agtcatcatc tcttgaaaga tgactctcca tagcctggg      59

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence:soluble
      epoxide hydrolase (sEH) target 4 for hairpin short or
      small interfering RNA (siRNA)

```
<400> SEQUENCE: 28
caagcagtgt tcattggcca tga                                          23

<210> SEQ ID NO 29
<211> LENGTH: 59
<212> TYPE: DNA
<213> ORGANISM: Artificial Sequence
<220> FEATURE:
<223> OTHER INFORMATION: Description of Artificial Sequence:soluble
      epoxide hydrolase (sEH) sense strand of hairpin short or
      small interfering RNA (siRNA) for target sequence 4

<400> SEQUENCE: 29
gatccccagc agtgttcatt ggccatttca agagaatggc caatgaacac tgctttttt   59

<210> SEQ ID NO 30
<211> LENGTH: 59
<212> TYPE: DNA
<213> ORGANISM: Artificial Sequence
<220> FEATURE:
<223> OTHER INFORMATION: Description of Artificial Sequence:soluble
      epoxide hydrolase (sEH) antisense strand of hairpin short or
      small interfering RNA (siRNA) for target sequence 4

<400> SEQUENCE: 30
agctaaaaaa gcagtgttca ttggccattc tcttgaaatg gccaatgaac actgctggg   59

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence:soluble
      epoxide hydrolase (sEH) target 5 for hairpin short or
      small interfering RNA (siRNA)

<400> SEQUENCE: 31
cagcacatgg aggactggat tcc                                          23

<210> SEQ ID NO 32
<211> LENGTH: 59
<212> TYPE: DNA
<213> ORGANISM: Artificial Sequence
<220> FEATURE:
<223> OTHER INFORMATION: Description of Artificial Sequence:soluble
      epoxide hydrolase (sEH) sense strand of hairpin short or
      small interfering RNA (siRNA) for target sequence 5

<400> SEQUENCE: 32
gatccccgca catggaggac tggattttca agagaaatcc agtcctccat gtgctttt    59

<210> SEQ ID NO 33
<211> LENGTH: 59
<212> TYPE: DNA
<213> ORGANISM: Artificial Sequence
<220> FEATURE:
<223> OTHER INFORMATION: Description of Artificial Sequence:soluble
      epoxide hydrolase (sEH) antisense strand of hairpin short or
      small interfering RNA (siRNA) for target sequence 5

<400> SEQUENCE: 33
agctaaaaag cacatggagg actggatttc tcttgaaaat ccagtcctcc atgtgcggg   59

<210> SEQ ID NO 34
<211> LENGTH: 20
<212> TYPE: RNA
<213> ORGANISM: Artificial Sequence
<220> FEATURE:
```

```
<223> OTHER INFORMATION: Description of Artificial Sequence:soluble
      epoxide hydrolase (sEH) exemplary antisense sequence 1

<400> SEQUENCE: 34
uguccagugc ccacaguccu                                             20

<210> SEQ ID NO 35
<211> LENGTH: 20
<212> TYPE: RNA
<213> ORGANISM: Artificial Sequence
<220> FEATURE:
<223> OTHER INFORMATION: Description of Artificial Sequence:soluble
      epoxide hydrolase (sEH) exemplary antisense sequence 2

<400> SEQUENCE: 35
uucccaccug acacgacucu                                             20

<210> SEQ ID NO 36
<211> LENGTH: 20
<212> TYPE: RNA
<213> ORGANISM: Artificial Sequence
<220> FEATURE:
<223> OTHER INFORMATION: Description of Artificial Sequence:soluble
      epoxide hydrolase (sEH) exemplary antisense sequence 3

<400> SEQUENCE: 36
guucagccuc agccacuccu                                             20

<210> SEQ ID NO 37
<211> LENGTH: 19
<212> TYPE: RNA
<213> ORGANISM: Artificial Sequence
<220> FEATURE:
<223> OTHER INFORMATION: Description of Artificial Sequence:soluble
      epoxide hydrolase (sEH) exemplary antisense sequence 4

<400> SEQUENCE: 37
aguccucccg cuucacaga                                              19

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence:soluble
      epoxide hydrolase (sEH) exemplary antisense sequence 5

<400> SEQUENCE: 38
gcccacuucc aguuccuuuc c                                           21
```

USE OF INHIBITORS OF SOLUBLE EPOXIDE HYDROLASE TO SYNERGIZE ACTIVITY OF COX AND 5-LOX INHIBITORS

CROSS-REFERENCES TO RELATED APPLICATIONS

This application claims priority from U.S. Provisional Application No. 60/643,028, filed Jan. 10, 2005, the contents of which are hereby incorporated by reference.

STATEMENT AS TO RIGHTS TO INVENTIONS MADE UNDER FEDERALLY SPONSORED RESEARCH AND DEVELOPMENT

This invention was made with government support under grant nos. R37 ES02710 and P01 ES04699, awarded by the National Institute of Environmental Health Sciences of the National Institutes of Health. The government has certain rights in the invention.

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Arachidonic acid is released from membrane phospholipids by the enzyme phospholipase A2. This highly unsaturated fatty acid is metabolized through one of three pathways: the cyclooxygenases ("COX"), the lipoxygenases ("LOX"), and the cytochrome P450 pathway. COX enzymes convert arachidonic acid to the prostaglandin endoperoxide PGH2, from which other prostaglandins are formed. See, e.g., Meade et al., J Biol. Chem. 274(12):8328-34 (1999). A number of drugs inhibit the action of either the COX or the LOX enzymes.

Non-steroidal anti-inflammatory drugs ("NSAIDs") are thought to exert their effect by primarily inhibiting the COX enzymes, thereby blocking production of prostaglandins and thromboxanes. The beneficial effects are thought to come from directly inhibiting $PGE_2$ and 5 other major metabolites. The titers of over 70 'by stander' eicosanoids, however, also are altered. Some of these eicosanoids are critical for normal physiology; thus, it has long been a goal to reduce the activity of COX enzymes associated with an over-active inflammatory response while not disturbing the normal functioning of approximately one-third of the carbon flow from arachidonic acid through the COX enzymes to prostaglandins and thromboxanes necessary for normal physiology.

Elucidation of the two COX isoforms COX-1 and COX-2 gave rise to the concept that the constitutive enzyme COX-1 was responsible for the production of prostaglandins and thromboxanes with homeostatic functions in platelets and such tissues as the stomach and kidney, while COX-2, the inducible enzyme, was reported for the production of prostaglandins involved in inflammation. See, e.g., Seibert and Masferrer, Receptor, 4:17 (1994). Accordingly, it was thought that the therapeutic effects of NSAIDs were attributable to the inhibition of COX-2, while the inhibition of COX-1 accounted for the adverse affects associated with these drugs. See, e.g., Lichtenstein et al., Arthritis Rheum 38:5 (1995). This is actually an oversimplification, because COX-2 is expressed constitutively in the brain, airway epithelium, prostate, and macula densa of the kidney.

Although NSAIDs are highly effective, their use is associated with a number of adverse effects such as gastrointestinal ulceration and bleeding, inhibition of platelet aggregation, and adverse changes in renal blood flow. Gastrointestinal toxicity associated with chronic NSAID used is estimated to result in more than 100,000 hospitalizations and 16,000 deaths per year in the U.S. alone. See, e.g., Singh and Tridafilopoulos, J. Rheumatol. Supp., 56:18 (1999). The side effects of such gastritis were thought to occur through COX-1 inhibition. This led to the development of selective COX-2 inhibitors to block the pro-inflammatory mediators and reduce the side effects of NSAIDs. These drugs (also known as "coxibs") are designed to specifically inhibit COX-2 and to have little effect on COX-1 activity across the therapeutic range. Examples of COX-2 inhibitors include celecoxib (Celebrex®, Pharmacia, Peapack, N.J.), refecoxib (Vioxx®, Merck, Whitehouse Station, N.J.), valdecoxib (Bextra®, Pfizer, New York, N.Y.), lumiracoxib (Prexige®, Novartis International AG, Basel, Switzerland), and etoricoxib (Arcoxia®, Merck, Whitehouse Station, N.J.).

Recent studies have challenged the hypothesis that COX-1 plays no role in inflammation and that COX-2 is the only isoform responsible for the synthesis of pro-inflammatory prostaglandins. In the rat carrageenin-induced pleurisy model, drugs more selective for COX-2 inhibition attenuated inflammation over wider time frame than selective COX-1 inhibitors, thus suggesting a role of COX-2 in this model. There is also increasing evidence that the inhibition of COX-2 delays the resolution of inflammation. Gilroy et al., FASEB J 15:288 (2001); Gilroy et al., Am J Physiol Cell Physiol 281:C188 (2001).

Despite their efficacy in the treatment of arthritic disease and chronic pain, NSAIDs are limited by their adverse drug interactions with anti-coagulants (e.g. warfarin) and anti-hypertensive drugs (e.g. angiotensin converting enzyme ("ACE") inhibitors). NSAIDs increase gastric irritation and erosion of the protective lining of the stomach, assisting in the formation of gastrointestinal bleeding. Additionally, NSAIDs decrease the cohesive properties of platelets necessary in clot formation; thus, the addition of warfarin can lead to coughing up blood, bleeding gums, and blood in urine and stool. A few patients treated with an angiotensin converting enzyme ("ACE") inhibitor and rofecoxib (Vioxx®), a selective COX-2 inhibitor, have developed serious renal problems that have led to severe hyperkalemia and death. Hay et al., J Emerg Med 22:349 (2002). Additionally, NSAIDs, especially aspirin, have been implicated in Reye's syndrome and in inducing asthmatic attacks in patients with asthma. This effect illustrates one of the problems in inhibiting either or both of the COX enzymes, because this inhibition shuttles arachidonate into other pathways in the arachidonate cascade, predominantly thought to be the LOX pathway. Increasing the flow of arachidonate through this pathway may itself result in undesirable side effects, including the production of pro-inflammatory mediators by the LOX enzymes, particularly 5-LOX.

Recently, some COX-2 inhibitors have been associated with higher risks for heart attacks or stroke. The associations are believed to be dose dependent. It has now been shown that selective COX-2 inhibitors depress $PGI_2$ without concomitant inhibition of $TXA_2$, which can result in an augmented response to thrombotic and hypertensive stimuli and acceleration of atherogenesis.

Epoxide hydrolases ("EHs") are enzymes that add water to epoxides, resulting in their corresponding 1,2-diols (Hammock, B. D. et al., in *Comprehensive Toxicology: Biotransformation* (Elsevier, New York), pp. 283-305 (1997); Oesch, F. Xenobiotica 3:305-340 (1972)). Four principal EH's are known: leukotriene epoxide hydrolase, cholesterol epoxide hydrolase, microsomal EH ("mEH"), and soluble EH ("sEH," previously called "cytosolic EH"). The leukotriene EH acts on leukotriene $A_4$, whereas the cholesterol EH hydrates compounds related to the 5,6-epoxide of cholesterol (Nashed, N. T., et al., Arch. Biochem. Biophysics., 241:149-162 (1985); Finley, B. and B. D. Hammock, Biochem. Pharmacol., 37:3169-3175 (1988)). The microsomal epoxide hydrolase metabolizes monosubstituted, 1,1-disubstituted, cisital-1,2-disubstituted epoxides and epoxides on cyclic systems epoxides to their corresponding diols. Because of its broad substrate specificity, this enzyme is thought to play a significant role in ameliorating epoxide toxicity. Reactions of detoxification typically decrease the hydrophobicity of a compound, resulting in a more polar and thereby excretable substance.

Soluble EH is only very distantly related to mEH and hydrates a wide range of epoxides not on cyclic systems. In contrast to the role played in the degradation of potential toxic epoxides by mEH, sEH is believed to play a role in the formation or degradation of endogenous chemical mediators. For instance, cytochrome P450 epoxygenase catalyzes NADPH-dependent enatioselective epoxidation of arachidonic acid to four optically active cis-epoxyeicosantrienoic acids ("EETs") (Karara, A., et al., J. Biol. Chem., 264:19822-19877 (1989)). Soluble epoxide hydrolase has been shown in vivo to convert these compounds with regio- and enantiofacial specificity to the corresponding vic-dihydroxyeicosatrienoic acids ("DHETs"). Both liver and lung cytosolic fraction hydrolyze 14,15-EET, 8,9-EET and 11,12-EET, in that order of preference. The 5,6 EET is hydrolyzed more slowly. Purified sEH selects 8S,9R- and 14R,15S-EET over their enantiomers as substrates. Studies have revealed that EETs and their corresponding DHETs exhibit a wide range of biological activities. Some of these activities include involvements in luteinizing hormone-releasing hormone, stimulation of luteinizing hormone release, inhibition of $Na^+/K^+$ ATPase, vasodilation of coronary artery, mobilization of $Ca^{2+}$ and inhibition of platelet aggregation.

BRIEF SUMMARY OF THE INVENTION

In a first group of embodiments, the invention provides compositions comprising a first enzyme inhibitor, which first enzyme inhibitor inhibits soluble epoxide hydrolase ("sEH"), and a second enzyme inhibitor, which second enzyme inhibitor inhibits one or more enzymes selected from the group consisting of cyclo-oxygenase ("COX")-1, COX-2, and 5-lipoxygenase ("5-LOX"). In some embodiments, the second enzyme inhibitor inhibits COX-2. In some embodiments, the second enzyme inhibitor is selected from the group consisting of celecoxib, valdecoxib, lumiracoxib, etoricoxib, and rofecoxib. In some embodiments, the second enzyme inhibitor is selected from the group of a direct inhibitor of 5-LOX and an inhibitor that inhibits 5-LOX by inhibiting 5-lipoxygenase activating protein. In some embodiments, the second inhibitor inhibits both COX-2 and 5-LOX. In some embodiments, the inhibitor of COX-2 and 5-LOX is selected from the group consisting of licofelone and tepoxalin. In some embodiments, the second enzyme inhibitor is selected from the group consisting of aspirin, acetaminophen, diclofenac potassium, diclofenac sodium, diclofenac sodium with misoprostol, diflunisal, etodolac, fenoprofen calcium, flurbiprofen, ibuprofen, indomethacin, ketoprofen, meclofenamate sodium, mefenamic acid, meloxicam, nabumetone, naproxen sodium, piroxicam, tolmetin sodium, magnesium salicylate, choline salicylate, salsalate, and sodium salicylate. In some embodiments, the composition further comprises a cis-epoxyeicosantrienoic acid. In some embodiments, the composition further comprises an epoxide of docosahexaenoic acid ("DHA") or eicosapentaenoic acid ("EPA"), or epoxides of both DHA and of EPA. In some embodiments, the first enzyme inhibitor has a primary pharmacophore selected from the group consisting of a urea, a carbamate, and an amide. In some embodiments, the first enzyme inhibitor further has a polyether secondary pharmacophore.

In some embodiments, the composition further comprises a pharmaceutically acceptable carrier. In some of these embodiments, the second enzyme inhibitor inhibits COX-2. In some of these embodiments, the second enzyme inhibitor inhibits 5-LOX. In some of these embodiments, the second enzyme inhibitor inhibits both COX-2 and 5-LOX. In some of these embodiments, the composition further comprises a cis-epoxyeicosantrienoic acid. In some of these embodiments, the first enzyme inhibitor has a primary pharmacophore selected from the group consisting of a urea, a carbamate and an amide. In some of these embodiments, the first enzyme inhibitor has a polyether secondary pharmacophore. In some of these embodiments, the second inhibitor is selected from the group consisting of aspirin, acetaminophen, diclofenac potassium, diclofenac sodium, diclofenac sodium with misoprostol, diflunisal, etodolac, fenoprofen calcium, flurbiprofen, ibuprofen, indomethacin, ketoprofen, meclofenamate sodium, mefenamic acid, meloxicam, nabumetone, naproxen sodium, piroxicam, tolmetin sodium, magnesium salicylate, choline salicylate, salsalate, and sodium salicylate.

In a further group of embodiments, the invention provides methods for increasing the effect in a subject of a first enzyme inhibitor having a residence time in the body, wherein the subject is administered a first enzyme inhibitor which first enzyme inhibitor inhibits the activity of an enzyme selected from the group consisting of: (a) cyclo-oxygenase ("COX")-1, COX-2,5-lipoxygenase ("5-LOX"), or a combination of these enzymes, and (b) soluble epoxide hydrolase ("sEH"), during the residence time of the first enzyme inhibitor in the body of the subject, the subject is administered a second enzyme inhibitor having a residence time in the body, which second enzyme inhibitor inhibits the activity of an enzyme selected from the group consisting of (c) COX-1, COX-2,5-LOX, or a combination of these enzymes, and (d) sEH, wherein the combination of said first and second enzyme inhibitors increases the effect of the first enzyme inhibitor over the effect of that inhibitor in the absence of the second enzyme inhibitor, provided that, when said first enzyme inhibitor is from group (a), said second enzyme inhibitor is from group (d) and when said first enzyme inhibitor is from group (b), said second enzyme inhibitor is from group (c). In some embodiments, the subject is administered the first enzyme inhibitor within 4 hours of the subject being administered the second enzyme inhibitor. In some embodiments, the inhibitor of COX-1, COX-2,5-LOX, or a combination of these enzymes is selected from the group consisting of celecoxib, valdecoxib, lumiracoxib, etoricoxib, rofecoxib and an inhibitor of 5-lipoxygenase activating protein. In some embodiments, the inhibitor of COX-1, COX-2,5-LOX, or a combination of these enzymes is selected from the group consisting of licofelone and tepoxalin. In some embodiments, the inhibitor of COX-1, COX-2,5-LOX, or a combination of these enzymes is selected from the group consisting of aspirin, acetaminophen, diclofenac potassium, diclofenac sodium, diclofenac sodium with misoprostol, diflunisal, etodolac, fenoprofen calcium, flurbiprofen, ibuprofen, indomethacin, ketoprofen, meclofenamate sodium, mefenamic acid, meloxicam, nabumetone, naproxen sodium, piroxicam, tolmetin sodium, magnesium salicylate, choline salicylate, salsalate, and sodium salicylate. In some embodiments, the inhibitor of sEH has a primary pharmacophore selected from the group consisting of a urea, a carbamate and an amide. In some embodiments, the inhibitor of sEH has a polyether secondary pharmacophore. In some embodiments, the method further comprises administering a cis-epoxyeicosantrienoic acid to said subject. In some embodiments, the method further comprises administering an epoxide of docosahexaenoic acid ("DHA") or of eicosapentaenoic acid ("EPA"), or an epoxide of DHA and an epoxide of EPA to said subject.

In a further group of embodiments, the invention provides methods of reducing pain in a subject, comprising administering to said subject an analgesic amount of an inhibitor of soluble epoxide hydrolase ("sEH"). In some embodiments, the inhibitor of sEH has a primary pharmacophore selected from the group consisting of a urea, a carbamate, and an amide. In some embodiments, the inhibitor of sEH has a polyether secondary pharmacophore. In some embodiments, the method futher comprises administering a cis-epoxyeicosantrienoic acid to the subject. In some embodiments, the method further comprises administering an inhibitor of an enzyme selected from the group consisting of cyclo-oxygenase ("COX")-1, COX-2, and 5-lipoxygenase ("5-LOX"). In some embodiments, the inhibitor of COX-1, COX-2, or 5-LOX is selected from the group consisting of celecoxib, valdecoxib, lumiracoxib, etoricoxib, rofecoxib, licofelone, tepoxalin, aspirin, acetaminophen, diclofenac potassium, diclofenac sodium, diclofenac sodium with misoprostol, diflunisal, etodolac, fenoprofen calcium, flurbiprofen, ibuprofen, indomethacin, ketoprofen, meclofenamate sodium, mefenamic acid, meloxicam, nabumetone, naproxen sodium, piroxicam, tolmetin sodium, magnesium salicylate, choline salicylate, salsalate, sodium salicylate, and an inhibitor of 5-lipoxygenase activating protein. In some embodiments, the method further comprises administering an epoxide of docosahexaenoic acid ("DHA") or of eicosapentaenoic acid ("EPA"), or an epoxide of DHA and an epoxide of EPA to said subject.

In yet a further group of embodiments, the invention provides methods of reducing pain or inflammation in a mammal in need thereof, said method comprising administering to said mammal an effective amount of an epoxide selected from the group consisting of an epoxide of eicosapentaenoic acid ("EPA") and an epoxide of docosahexaenoic acid ("DHA"), thereby reducing said pain or inflammation. In some embodiments, the epoxide is an epoxide of EPA. In some embodiments, the epoxide is an epoxide of DHA. In some embodiments, the method comprises administering both an epoxide of EPA and an epoxide of DHA. In some embodiments, the method further comprises administering an inhibitor of soluble epoxide hydrolase.

In still another group of embodiments, the invention provides compositions comprising (a) an epoxide selected from the group consisting of an epoxide of eicosapentaenoic acid ("EPA") and an epoxide of docosahexaenoic acid ("DHA"), and (b) a pharmaceutically acceptable carrier or excipient. In some embodiments, the epoxide is an epoxide of EPA. In some embodiments, the epoxide is an epoxide of DHA. In some embodiments, the composition comprises both an epoxide of EPA and an epoxide of DHA. In some embodiments, the composition further comprises an inhibitor of soluble epoxide hydrolase.

DETAILED DESCRIPTION OF THE INVENTION

Figure 1:
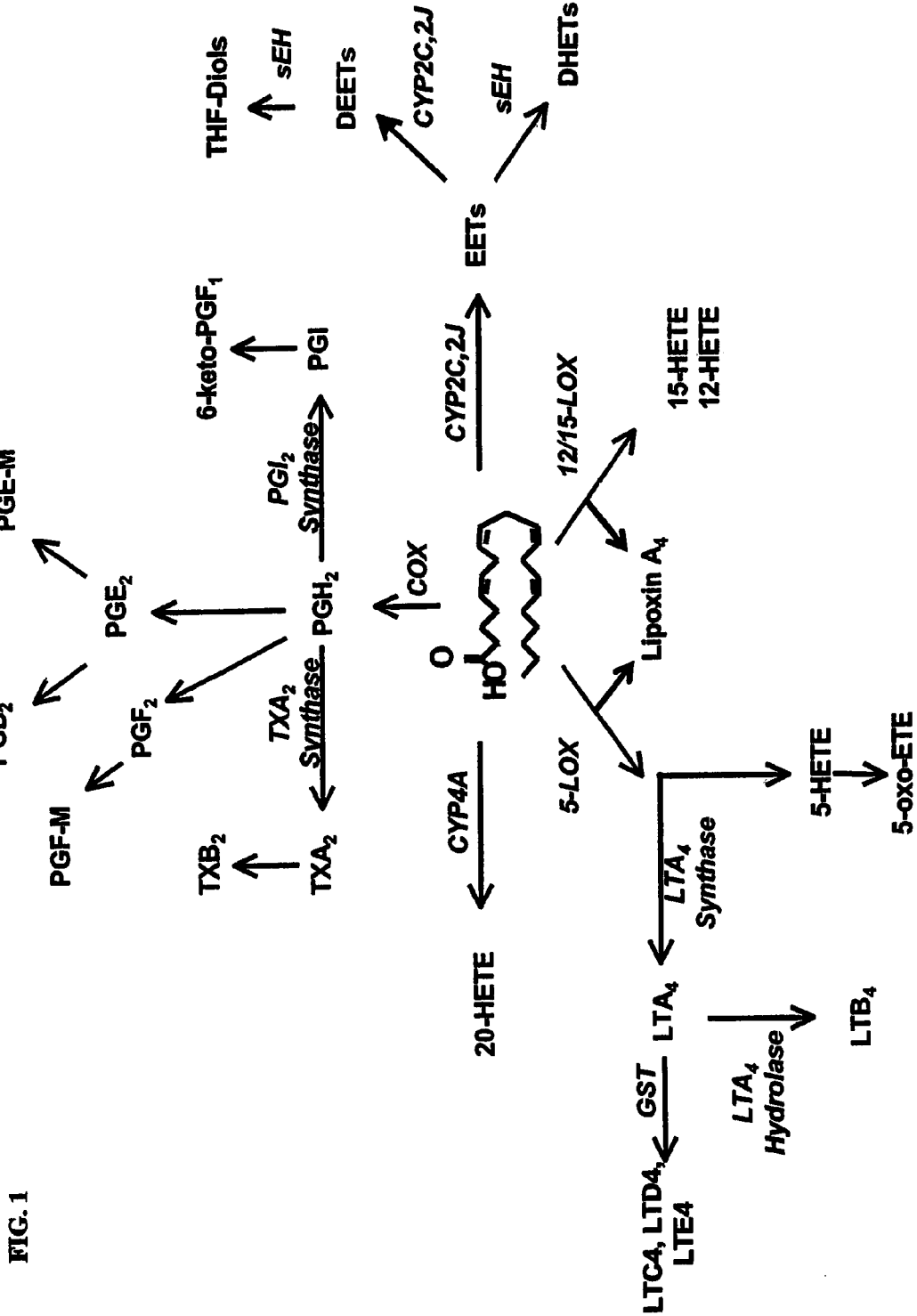
FIG. 1 is a illustration of the cascades by which arachidonic acid is metabolized in the body. "5-LOX" is the pro-inflammatory enzyme arachidonate 5-lipoxygenase. "COX" is the cyclooxygenase pathway. "CYP4A" is cytochrome P450 4A. "CYP2C" is cytochrome P450 2C. "sEH" is soluble epoxide hydrolase.

I. Introduction
A. COX, LOX, and sEH

Inhibition of the enzyme known as "soluble epoxide hydrolase" ("sEH") reduces inflammation. See, U.S. Pat. No. 6,150,415. Cis-Epoxyeicosatrienoic acids ("EETs") are substrates sEH hydrolyzes; it is in part the increase in the levels of EETs by inhibiting sEH that results in the anti-inflammatory effect seen when sEH inhibitors ("sEHIs") are administered.

Surprisingly, we have now discovered that inhibition of COX-1 and COX-2 results in a rise in EET levels. This effect has not previously been recognized, and leads us to conclude that some or all of the anti-inflammatory effect and analgesic effects seen from the use of COX-1 and COX-2 inhibitors result only not only from blocking the formation of prostaglandins and other downstream, pro-inflammatory metabolites, as has been believed in the art, but also from the rise in EET levels. Further, the studies underlying the present invention reveal that the rise in levels of EETs from the action of inhibitors of COX-1 or COX-2 further increases dramatically in the presence of sEHIs.

The discoveries underlying the present invention have several related implications. First, to the extent that the analgesic effects of COX-1 and -2 inhibitors are due to their effect on increasing the levels of EETs, sEHI's, which also increase the levels of EETs in the body, are also analgesics. This analgesic property of sEHIs has been previously unrecognized. Compounds which stabilize EETs or which mimic them are likewise expected to have analgesic properties, either by acting as EETs or by acting as a decoy for sEH, thereby reducing the rate at which endogenous EETs are hydrolyzed and maintaining their levels in the body for a longer period.

The analgesic effect of EETs and their mimics is augmented by the fact that EETs are believed to inhibit activation of nuclear factor κB (NF-κB) and to inhibit the nuclear translocation of NF-κB. This in turn reduces activation of a variety of proinflammatory peptides and proteins, such as COX-2. Our studies indicate that COX-2 levels are reduced at 6, 12, and 24 hours after exposure to inflammation mediators when sEHIs are administered. Thus, in addition to the direct effect on reducing pain and inflammation due to increasing the level of EETs, sEHIs also reduce pain and inflammation indirectly at the level of transcription and protein induction. Because the rate at which EETs are degraded is reduced by the presence of the sEHIs, the analgesic effect can be increased by administering EETs with or in conjunction with the sEHI.

Second, the dramatic increases in EET levels seen when both a COX inhibitor and a sEHI are co-administered indicate that sEHI's act synergistically with inhibitors of COX-1 and of COX-2 in increasing EET levels. As noted, we have discovered that COX-1 and COX-2 inhibitors increase the levels of EETs present in the body. The presence of sEHIs slows the hydrolysis of the EETs to their corresponding diols, thereby increasing the effect of the COX inhibitors. Any given dosage of the COX-1 or COX-2 inhibitor will therefore have a stronger effect, and a lower dosage will be needed to achieve a given reduction in pain or inflammation. For example, in an animal model, a combination 10 mg/Kg ("mpk") of the COX-2 inhibitor Vioxx® and 20 mg/Kg of the sEH inhibitor ("sEHI") AUDA-BE caused a reduction in pain equivalent to that of 25 mg/Kg of Vioxx® administered by itself. See, Example 8 and FIG. 6. Since the side effects of COX-2 inhibitors are considered to be dose related, the ability to be able to reduce the dosage of COX-2 inhibitor necessary to achieve any given amount of pain relief also reduces the side effects related to use of the COX-2 inhibitor. As reported in the Examples, studies of the effects of co-administering COX-2 inhibitors and sEHI resulted in lowering the levels of metabolites considered to be indicators of increased risk of heart attack or stroke.

The joint effect of both a COX inhibitor and an sEHI should be generally applicable to downstream metabolites of epoxy-lipins not involving diol formation. As will be explained in more detail below, and without wishing to be bound by theory, it is believed that the sEHI and the COX inhibitors act by two separate mechanisms. Again without wishing to be bound by theory, it is believed that the combination of the two mechanisms is responsible at least in part for the synergistic effects on pain and inflammation seen in combining the two different types of inhibitors.

As noted, EETs inhibit the activation and nuclear translocation of NF-κB. This in turn reduces activation of a variety of proinflammatory peptides and proteins, such as COX-2. Thus, the sEHIs reduce the amount of COX-2 present and this, in turn, reduces the amount of inhibitor of COX-2 needed to block the formation of pro-inflammatory metabolites. The use of sEHIs in conjunction with a COX-1 or COX-2 inhibitor, or both, therefore improves the anti-inflammatory effects of the COX-1 or COX-2 inhibitor, while simultaneously reducing the side effects associated with the COX-1 or COX-2 inhibitor.

Third, another group of enzymes involved in arachidonic acid metabolism are the lipoxygenases ("LOX"). The LOX enzymes, and especially the enzyme known as "5-LOX", are implicated in inflammation through their activation of proinflammatory substances called leukotrienes. In the absence of sEHIs, the inhibition of COX enzymes results in increasing the flow of arachidonic acid metabolites through the LOX pathway, and increases the production of the pro-inflammatory leukotrienes. Similarly, it is believed that inhibition of the LOX pathway shuttles more arachidonate into other pathways in the arachidonate cascade, including the COX pathways, leading to increased amounts of inflammatory mediators. Thus, the use of sEHIs in conjunction with an inhibitor of 5-LOX can potentiate the anti-inflammatory effects of the LOX inhibitor, while simultaneously reducing its side effects. One of the factors in the activation of 5-LOX is 5-lipoxygenase activating protein, usually abbreviated as "FLAP." Inhibitors of FLAP, such as MK886 (Merck Co., Darm-stadt, Germany), DG-031 (Decode Genetics Inc., Reykjavik, Iceland), and BAY X 1005 ((R)-2-[4-(quinolin-2-yl-methoxy) phenyl]-2-cyclopentyl acetic acid, Bayer AG, Leverkusen, Germany). See, e.g., Harkonarson et al., JAMA, 293(18): 2277-9 (2005), Mancini et al., J Biol Chem, 273(49):32842-32847 (1998); Burchhardt and Muller-Peddinghaus, Prostaglandins Leukot Essent Fatty Acids. 60(1):5-11 (1999); Hatzelmann et al., Biochem Pharmacol. 45(1):101-11 (1993); Titos et al., FASEB J. 17:1745-1747 (2003). Thus, 5-LOX can be inhibited directly by a 5-LOX inhibitor, or indirectly, by inhibiting FLAP, which would otherwise activate 5-LOX.

The compositions and methods of the invention have a number of benefits. First, the methods and compositions elevate mediators with favorable effects and, to the extent that they reduce the formation of COX, reduce the production of pro-inflammatory metabolites. Second, the metabolites of sEH are not known to have significant roles in controlling homeostasis. Thus, the adverse side effects and adverse drug interactions seen in directly inhibiting COX-2 is not a factor with the use of sEHI. Third, whereas it has recently been noted that COX-2 inhibitors delay the resolution of inflammation, sEHI are believed to induce the formation of the pro-resolution lipid mediator Lipoxin $A_4$. Therefore, use of sEHI in combination with COX-1, COX-2, or 5-LOX inhibitors are expected to reduce pro-inflammatory gene and protein expression, while promoting healing. Further, recent reports have indicated that high levels of COX inhibitors are linked to increased risk of heart attack or stroke, and have led to a reduced use of COX inhibitors. The discoveries of the invention indicate that COX inhibitors can be effective at lower levels, diminishing the risk to the patient.

Persons of skill will appreciate that, while the pharmacokinetics of drugs vary, there is typically a lag after a drug is administered to before the drug reaches a therapeutically effective level, after which the concentration of the drug in the body reaches a maximum, and then diminishes as the drug is metabolized, excreted or eliminated. The time course of a drug in the body is routinely studied in pre-clinical studies and during clinical trials. For convenience of reference, the time between administration of a drug and its being metabolized or eliminated may be referred to as its residence time in the body.

It will be recognized that, for a sEHI to enhance the effect of a COX or LOX inhibitor in a subject, it is preferred if the sEHI is present in the subject's body at the same time as the COX or the LOX inhibitor. Thus, it is preferable that the sEHI be administered with the COX or LOX inhibitor, either individually or in a combination form, such as a tablet. If desired, however, the sEHI can be administered before or after the COX or LOX inhibitor, so long as the residence time of the sEHI and that of the COX or LOX inhibitor overlap. Thus, for example, if the COX or LOX inhibitor has a residence time of 4 hours, the sEHI should be administered within 4 hours before or after administration of the COX or LOX inhibitor so that the residence times of the two enzyme inhibitors overlap.

Surprisingly, the recognition that COX inhibitors increases EET levels indicates that some or all of the analgesic effect of COX inhibitors is due to this effect. In light of this finding, it is therefore expected that sEHIs themselves have an analgesic effect, and can reduce or prevent pain independently of their effect on reducing inflammation or hypertension or, indeed, on the various other conditions (e.g., diabetic nephropathy, stroke, chronic obstructive pulmonary disease, proliferation of vascular smooth muscle cells, type 1 and type 2 diabetes, insulin resistance syndrome, hypertension, atherosclerosis, coronary artery disease, angina, ischemia, ischemic stroke, Raynaud's disease and renal disease), on which sEHIs have previously been predicted to have an effect. It will also be appreciated that there are many sources of pain not related to the conditions with which sEHIs have previously been associated, such as tension headaches, and chronic back pain, for which sEHIs can be used to relieve pain.

Accordingly, while sEHIs can be used to alleviate pain from conditions with which sEHIs have already be shown or predicted to have an effect, sEHI can also be used to alleviate pain that is not associated with inflammation or other conditions previously identified as benefiting from treatment with sEHI, including those listed above. Persons of skill will recognize that the measurement of pain, and of its reduction or alleviation by various compounds, has been practiced for years. Accordingly, assays and procedures known in the art can be used to demonstrate pain reduction by sEHI. Exemplary assays for determining analgesic properties are set forth in the Examples, below. Studies of two sEHI in animal models demonstrated that the sEHI had an analgesic effect. Further, studies in an animal model showed that animals pretreated with a COX-2 inhibitor and an sEHI, showed increased tolerance to pain compared to animals treated with the same dose of the COX-2 inhibitor without the sEHI. See, FIG. 6 and Example 8.

The studies reported herein show that the administration of sEHI and a COX-2 inhibitor to an animal subjected to LPS, an inflammatory stimulus, notably reduced the production of the metabolites $PGD_2$ and $PGE_2$. compared to the production of the metabolites when animals were administered the same amount of the same COX-2 inhibitor without the sEHI. See, e.g., FIG. 5. These unexpected results are believed to be due to the fact that we are targeting the COX-2 enzyme by reducing the amount of COX-2 induced, via NFkB, and then directly inhibiting the COX-2 that is already present, via a low dose of a COX-2 inhibitor.

Current reports in the literature indicate that COX-2 is expressed constitutively in the heart, lungs, and gastrointestinal tract, while higher levels are induced in other tissues and cell types. As numerous reports have shown, COX-2 inhibitors inhibit the activity of the enzyme. The data from the present studies suggest that COX-2 inhibitors do not reduce the induction of COX-2 in response to an inflammatory stimulus. This is shown graphically in FIG. 8, in which the bar for the COX-2 level in livers of animals administered the inflammatory agent lipopolysaccharide ("LPS") in vehicle is roughly equivalent to the bar depicting the COX-2 level in livers of animals administered 50 mg/Kg of a COX-2 inhibitor and within the error bar of the bar depicting the COX-2 level in livers of animals administered 100 mg/Kg of the same COX-2 inhibitor. In contrast, sEHI do not directly inhibit COX-2 activity in in vitro studies. As graphically shown in FIG. 8, however, they reduce the level of induction of COX-2 by some 30-40% compared to the induction seen when animals are subjected to the same inflammatory agent in the same amount, and do not reduce constitutive expression of COX-2. Thus, sEHI can be administered without the side effects that COX-2 inhibitors have shown. And, as noted above, since the combination of an sEHI and a COX-2 inhibitor permits achieving a given amount of effect (such as a given amount of pain relief) with a lower level of COX-2 inhibitor than would be necessary in the absence of the sEHI, the use of the combination reduces the side effects that would otherwise be due to the amount of COX-2 inhibitor that would otherwise be necessary to achieve the same result.

COX-2 inhibitors and sEHI reduce inflammation by different means. COX-2 inhibitors are known to inhibit COX-2 activity, while sEHI do not directly inhibit the activity of COX-2, but reduce the amount of COX-2 that would otherwise be inducted by inflammatory agents. As noted above, without wishing to be bound by theory, these different mechanisms of action, previously unknown, may be responsible in part for the synergistic effects seen in combining the use of the two types of agents.

As noted above, the sEHI was shown to reduce the induction of COX-2 by the inflammatory agent, LPS. It was expected that, since the COX-2 inhibitor did not reduce the amount of COX-2 induced by LPS, adding the COX-2 inhibitor to the sEHI would result in the same level of induction of COX-2 as that seen with the use of the sEHI alone. To our surprise, the combination of the COX-2 inhibitor and the exemplar sEHI resulted in a lower induction of COX-2 by LPS than the level induced in the presence of the sEHI and LPS without the COX-2 inhibitor. It should be noted that, although the Figure reports only the results of studies using the COX-2 inhibitor Celebrex® (celecoxib), the study was repeated using the COX-2 inhibitor Vioxx® and the COX1/2 inhibitor Indomethacin, as well as the polyether sEHI known as compound 950. Each study gave results similar to those shown in FIG. 8.

It should be noted that curcumin, present in tumeric and commercial mustards, has been reported to reduce COX-2 expression and activity in vitro, and has been reported to slow the growth of some cancer cell lines. Tablets containing curcumin are commercially available. Thus, persons eating dishes containing tumeric or mustard, or taking curcumin in tablets may have been ingesting levels of curcumin helpful in reducing COX-2 expression or activity. Further, a plant used in traditional Chinese herbal medicine, known as "Thunder God Vine" (*Tripterygium wilfordii*), has been reported to have some effect on COX-2 expression. In preferred embodiments, the methods of the invention reciting the use of a COX-2 inhibitor do not refer to the use of food as the COX-2 inhibitor. Nor, in preferred embodiments, do they refer to curcumin tablets or capsules as the COX-2 inhibitor, unless the curcumin is combined in the capsule or the tablet with a sEHI.

In some embodiments in which an inhibitor of FLAP and an sEHI are administered to an individual, the individual has preferably not taken a FLAP inhibitor for Alzheimer's disease, brain ischemia, traumatic brain injury, Parkinson's Disease, Multiple Sclerosis, ALS, subarachnoid hemorrhage or another disorder associated with excessive production of inflammatory mediators in the brain. In some embodiments, the person receiving the sEHI is not also taking an sEHI for a disease or condition caused by an autoimmune disease or a disorder associated with a T-lymphocyte mediated immune function autoimmune response. In some embodiments, the patient does not also have a pathological condition selected from type 1 or type 2 diabetes, insulin resistance syndrome, atherosclerosis, coronary artery disease, angina, ischemia, ischemic stroke, Raynaud's disease, or renal disease. In some embodiments, the patient is not a person with diabetes mellitus whose blood pressure is 130/80 or less, a person with metabolic syndrome whose blood pressure is less than 130/85, a person with a triglyceride level over 215 mg/dL, or a person with a cholesterol level over 200 mg/dL or is a person with one or more of these conditions who is not taking an inhibitor of sEH. In some embodiments, the patient does not have an obstructive pulmonary disease, an interstitial lung disease, or asthma. In some embodiments, the patient does not have cardiomyopathy or glaucoma.

B. EETs

EETs are epoxides of arachidonic acid known to be effectors of blood pressure, regulators of inflammation, and modulators of vascular permeability. Hydrolysis of the epoxides by sEH diminishes this activity. Inhibition of sEH raises the level of EETs since the rate at which the EETs are hydrolyzed into DHETs is reduced.

EETs have not generally previously been administered therapeutically, largely because it has been believed they would be hydrolyzed too quickly by endogenous sEH to be helpful. It was not known whether endogenous sEH could be inhibited sufficiently in the body to permit administration of exogenous EET to result in increased levels of EETs over those normally present. Recent studies, reported in co-owned application U.S. Ser. No. 10/815,425, showed that administration of EETs in conjunction with inhibitors of sEH to rats exposed to tobacco smoke resulted in reduced levels of recruitment of white blood cells in the lungs than did administration of sEH inhibitors alone. The results indicate that the combination of the two agents was more powerful in reducing tobacco smoke-related irritation to the lung than administration of an sEH inhibitor by itself. These studies evidence that EETs administered in conjunction with inhibitors of sEH increase the therapeutic effect over that of the sEH inhibitor alone.

The fact that EET levels can be raised by use of sEHIs indicates that the beneficial effect of sEHIs in enhancing the activities of COX and LOX inhibitors can be further augmented by administering EETs during the period effective amounts of sEHIs are present.

EETs useful in the methods of the present invention include 14,15-EET, 8,9-EET and 11,12-EET, and 5,6 EETs, in that order of preference. Preferably, the EETs are administered as the methyl ester, which is more stable. Persons of skill will recognize that the EETs are regioisomers, such as 8S,9R- and 14R,15S-EET. 8,9-EET, 11,12-EET, and 14R,15S-EET, are commercially available from, for example, Sigma-Aldrich (catalog nos. E5516, E5641, and E5766, respectively, Sigma-Aldrich Corp., St. Louis, Mo.).

Persons of skill will recognize that modifying an EET to reduce its hydrolysis by sEH will increase its metabolic stability and thus prolong its beneficial effects. These "mimics" of EETs are therefore advantageous. The term EETs as used herein therefore refers narrowly to the EETs described above, but also more broadly to mimics of EETs that are metabolically stable, that is, that are more resistant to hydrolysis by sEH than are natural EETs.

C. Epoxides of EPA and DRA

The fatty acids eicosapentaenoic acid ("EPA") and docosahexaenoic acid ("DHA") have recently become recognized as having beneficial effects, and fish oil tablets, which are a good source of these fatty acids, are widely sold as supplements. In 2003, it was reported that these fatty acids reduced pain and inflammation. Sethi, S. et al., Blood 100: 1340-1346 (2002). The paper did not identify the mechanism of action, nor the agents responsible for this relief.

Cytochrome P450 ("CYP450") metabolism produces cis-epoxydocosapentaenoic acids ("EpDPEs") and cis-epoxyeicosatetraenoic acids ("EpETEs") from docosahexaenoic acid ("DHA") and eicosapentaenoic acid ("EPA"), respectively. These epoxides are known endothelium-derived hyperpolarizing factors ("EDHFs"). These EDHFs, and others yet unidentified, are mediators released from vascular endothelial cells in response to acetylcholine and bradykinin, and are distinct from the NOS- (nitric oxide) and COX-derived (prostacyclin) vasodilators. Overall cytochrome P450 (CYP450) metabolism of polyunsaturated fatty acids produces epoxides, such as EETs, which are prime candidates for the active mediator(s). 14(15)-EpETE, for example, is derived via epoxidation of the 14,15-double bond of EPA and is the ω-3 homolog of 14(15)-EpETrE ("14(15)EET") derived via epoxidation of the 14,15-double bond of arachidonic acid.

As mentioned, we have found that it is beneficial to elevate the levels of EETs, which are epoxides of the fatty acid arachidonic acid. Our studies of the effects of EETs has led us to realization that the anti-inflammatory effect of EPA and DHA are likely due to increasing the levels of the epoxides of these two fatty acids. Thus, we expect that increasing the levels of epoxides of EPA, of DHA, or of both, will act to reduce pain and inflammation in mammals in need thereof. This beneficial effect of the epoxides of these fatty acids has not been previously recognized. Moreover, these epoxides have not previously been administered as agents, in part because, as noted above, epoxides have generally been considered too labile to be administered.

Like EETs, the epoxides of EPA and DHA are substrates for sEH. The epoxides of EPA and DHA are produced in the body at low levels by the action of cytochrome P450s. Endogenous levels of these epoxides can be maintained or increased by the administration of sEHI. However, the endogeous production of these epoxides is low and usually occurs in relatively special circumstances, such as the resolution of inflammation. Our expectation is that administering these epoxides from exogenous sources will aid in the resolution of inflammation and in reducing pain. We further expect that it will be beneficial with pain or inflammation to inhibit sEH with sEHI to reduce hydrolysis of these epoxides, thereby maintaining them at relatively high levels.

EPA has five unsaturated bonds, and thus five positions at which epoxides can be formed, while DHA has six. The epoxides of EPA are typically abbreviated and referred to generically as "EpETEs", while the epoxides of DHA are typically abbreviated and referred to generically as "EpDPEs". The specific regioisomers of the epoxides of each fatty acid are set forth in the following Table:

TABLE A

Regioisomers of Eicosapentaenoic acid ("EPA") epoxides:

1. Formal name: (±)5(6)-epoxy-8Z,11Z,14Z,17Z-eicosatetraenoic acid,
   Synonym 5(6)-epoxy Eicosatetraenoic acid
   Abbreviation 5(6)-EpETE
2. Formal name: (±)8(9)-epoxy-5Z,11Z,14Z,17Z-eicosatetraenoic acid,
   Synonym 8(9)-epoxy Eicosatetraenoic acid
   Abbreviation 8(9)-EpETE
3. Formal name: (±)11(12)-epoxy-5Z,8Z,14Z,17Z-eicosatetraenoic acid,
   Synonym 11(12)-epoxy Eicosatetraenoic acid
   Abbreviation 11(12)-EpETE
4. Formal name: (±)14(15)-epoxy-5Z,8Z,11Z,17Z-eicosatetraenoic acid,
   Synonym 14(15)-epoxy Eicosatetraenoic acid
   Abbreviation 14(15)-EpETE
5. Formal name: (±)17(18)-epoxy-5Z,8Z,11Z,14Z-eicosatetraenoic acid,
   Synonym 17(18)-epoxy Eicosatetraenoic acid
   Abbreviation 17(18)-EpETE Regioisomers of Docosahexaenoic acid ("DHA") epoxides:

TABLE A-continued

1. Formal name: (±)4(5)-epoxy-7Z,10Z,13Z,16Z,19Z-docosapentaenoic acid,
   Synonym 4(5)-epoxy Docosapentaenoic acid
   Abbreviation 4(5)-EpDPE
2. Formal name: (±)7(8)-epoxy-4Z,10Z,13Z,16Z,19Z-docosapentaenoic acid,
   Synonym 7(8)-epoxy Docosapentaenoic acid
   Abbreviation 7(8)-EpDPE
3. Formal name: (±)10(11)-epoxy-4Z,7Z,13Z,16Z,19Z-docosapentaenoic acid,
   Synonym 10(11)-epoxy Docosapentaenoic acid
   Abbreviation 10(11)-EpDPE
4. Formal name: (±)13(14)-epoxy-4Z,7Z,10Z,16Z,19Z-docosapentaenoic acid,
   Synonym 13(14)-epoxy Docosapentaenoic acid
   Abbreviation 13(14)-EpDPE
5. Formal name: (±)16(17)-epoxy-4Z,7Z,10Z,13Z,19Z-docosapentaenoic acid,
   Synonym 16(17)-epoxy Docosapentaenoic acid
   Abbreviation 16(17)-EpDPE
6. Formal name: (±)19(20)-epoxy-4Z,7Z,10Z,13Z,16Z-docosapentaenoic acid,
   Synonym 19(20)-epoxy Docosapentaenoic acid
   Abbreviation 19(20)-EpDPE Any of these epoxides, or combinations of any of these, can be administered in the compositions and methods of the invention.

II. Definitions

Units, prefixes, and symbols are denoted in their Systéme International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the invention, which can be had by reference to the specification as a whole. Accordingly, the terms defined immediately below are more fully defined by reference to the specification in its entirety. Terms not defined herein have their ordinary meaning as understood by a person of skill in the art.

"Epoxide hydrolases" ("EH;" IUBMB Enzyme Nomenclature EC 3.3.2.3) are enzymes in the alpha beta hydrolase fold family that add water to 3 membered cyclic ethers termed "epoxides."

"Soluble epoxide hydrolase" ("sEH") is an enzyme which in endothelial and smooth muscle cells converts EETs to dihydroxy derivatives called dihydroxyeicosatrienoic acids ("DHETs"). The cloning and sequence of the murine sEH is set forth in Grant et al., J. Biol. Chem. 268(23):17628-17633 (1993). The cloning, sequence, and accession numbers of the human sEH sequence are set forth in Beetham et al., Arch. Biochem. Biophys. 305(1):197-201 (1993). The amino acid sequence of human sEH is also set forth as SEQ ID NO:2 of U.S. Pat. No. 5,445,956; the nucleic acid sequence encoding the human sEH is set forth as nucleotides 42-1703 of SEQ ID NO:1 of that patent. The evolution and nomenclature of the gene is discussed in Beetham et al., DNA Cell Biol. 14(1): 61-71 (1995). Soluble epoxide hydrolase represents a single highly conserved gene product with over 90% homology between rodent and human (Arand et al., FEBS Lett., 338: 251-256 (1994)). Unless otherwise specified, as used herein, the terms "soluble epoxide hydrolase" and "sEH" refer to human sEH.

Unless otherwise specified, as used herein, the term "sEH inhibitor" (sometimes abbreviated herein as "sEHI") refers to an inhibitor of human sEH. Preferably, the inhibitor does not also inhibit the activity of microsomal epoxide hydrolase ("mEH") by more than 25% at concentrations at which the inhibitor inhibits sEH by at least 50%, and more preferably does not inhibit mEH by more than 10% at that concentration. For convenience of reference, unless otherwise required by context, the term "sEH inhibitor" as used herein encompasses prodrugs which are metabolized to active inhibitors of sEH. Further for convenience of reference, except as otherwise required by context, reference herein to a compound as an inhibitor of sEH includes reference to derivatives of that compound (such as an ester of that compound) that retain activity as an sEH inhibitor.

"COX" is an abbreviation for "cyclo-oxygenase." Several COX enzymes have been identified. Two isozymes, COX-1 and COX-2, are recognized as of clinical significance, with COX-1 considered to be constitutively expressed and COX-2 considered to be inducible and more prevalent at sites of inflammation. See, e.g., Hawkey, Best Pract Res Clin Gastroenterol. 15(5):801-20 (2001).

As used herein, a "COX-1 inhibitor" denotes an agent that inhibits COX-1 more than it inhibits COX-2, while a "COX-2 inhibitor" denotes an agent that inhibits COX-2 more than it inhibits COX-1. All current non-steroidal anti-inflammatory drugs (NSAIDs) inhibit both COX-1 and COX-2, but most tend to inhibit the two isoforms to different degrees. Since both enzymes tend to be inhibited together to some degree, one can consider an inhibitor of either enzyme to be "COX inhibitor".

"LOX" is an abbreviation for "lipoxygenase." Several LOX enzymes have been identified. Arachidonate 5-lipoxygenase ("5-LOX", EC 1.13.11.34) is involved in the production of pro-inflammatory mediators. Arachidonate 12-lipoxygenase ("12-LOX", EC 1.13.11.31) and arachidonate 15-lipoxygenase ("15-LOX", EC 1.13.11.33) form trihydroxytetraenes known as "lipoxins" ("lipoxygenase interaction products") from arachidonic acid. Lipoxins act as local anti-inflammatory agents.

"5-lipoxygenase activating protein," or "FLAP," is a protein required before 5-LOX can become catalytically active. Inhibiting FLAP activity reduces or prevents 5-LOX activation, decreasing the biosynthesis of leukotrienes.

"cis-Epoxyeicosatrienoic acids" ("EETs") are biomediators synthesized by cytochrome P450 epoxygenases. EETs are hydrolyzed by sEH to the corresponding diols, which are dihydroxyeicosatrienoic acids ("DHETs"). As noted above, modifying an EET to reduce its hydrolysis by sEH will increase its metabolic stability and thus prolong its beneficial effects. The term EETs as used herein therefore refers narrowly to the EETs described above, but also more broadly to mimics of EETs that are metabolically stable, that is, that are more resistant to hydrolysis by sEH than are natural EETs.

Cytochrome P450 ("CYP450") metabolism produces cis-epoxydocosapentaenoic acids ("EpDPEs") and cis-epoxyeicosatetraenoic acids ("EpETEs") from docosahexaenoic acid ("DHA") and eicosapentaenoic acid ("EPA"), respectively. These epoxides are known endothelium-derived hyperpolarizing factors ("EDHFs"). These EDHFs, and others yet unidentified, are mediators released from vascular endothelial cells in response to acetylcholine and bradykinin, and are distinct from the NOS- (nitric oxide) and COX-derived (prostacyclin) vasodilators. Overall cytochrome P450 (CYP450) metabolism of polyunsaturated fatty acids produces epoxides, such as EETs, which are prime candidates for the active mediator(s). 14(15)-EpETE, for example, is derived via epoxidation of the 14,15-double bond of EPA and is the ω-3 homolog of 14(15)-EpETrE ("14(15)EET") derived via epoxidation of the 14,15-double bond of arachidonic acid.

"$IC_{50}$" refers to the concentration of an agent required to inhibit enzyme activity by 50%.

By "physiological conditions" is meant an extracellular milieu having conditions (e.g., temperature, pH, and osmolarity) which allows for the sustenance or growth of a cell of interest.

The term "therapeutically effective amount" refers to that amount of the compound being administered sufficient to prevent or decrease the development of one or more of the symptoms of the disease, condition or disorder being treated.

The term "analgesic amount" refers to that amount of the compound being administered sufficient to prevent or decrease pain in a subject under treatment.

The term "modulate" refers to the ability of a compound to increase or decrease the function, or activity, of the associated activity (e.g., soluble epoxide hydrolase). "Modulation," as used herein in its various forms, is meant to include antagonism and partial antagonism of the activity associated with sEH. Inhibitors of sEH are compounds that, e.g., bind to, partially or totally block the enzyme's activity.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof. [0040] The "subject" is defined herein to include animals such as mammals, including, but not limited to, primates (e.g., humans), cows, sheep, goats, horses, dogs, cats, rabbits, rats, mice and the like. In preferred embodiments, the subject is a human.

Unless otherwise required by context, "administering" an EET, an EpETE, or a EpDPE, and an sEH inhibitor to a person in need thereof includes administering an sEH inhibitor, followed by a later administration of an EET, EpETE, or EpDPE, while an amount of sEH inhibitor is still present sufficient to reduce by at least 25% the rate of hydrolysis of the epoxide by sEH.

III. COX-1 and COX-2 Inhibitors

All current non-steroidal anti-inflammatory drugs (NSAIDs) inhibit both isoforms, but most tend to inhibit the two isoforms to different degrees. Since COX-2 is considered the enzyme associated with an inflammatory response, enzyme selectivity is generally measured in terms of specificity for COX-2. Typically, cells of a target organ that express COX-1 or COX-2 are exposed to increasing levels of NSAIDs. If the cell does not normally produce COX-2, COX-2 is induced by a stimulant, usually bacterial lipopolysaccharide (LPS).

The relative activity of NSAIDs on COX-1 and COX-2 is expressed by the ratio of $IC_{50}$s for each enzyme: COX-2 ($IC_{50}$)/COX-1 ($IC_{50}$). The smaller the ratio, the more specific the NSAID is for COX-2. For example, various NSAIDs have been reported to have ratios of COX-2 ($IC_{50}$)/COX-1 ($IC_{50}$) ranging from 0.33 to 122. See, Englehart et al., J Inflammatory Res 44:422-33 (1995). Aspirin has an $IC_{50}$ ratio of 0.32, indicating that it inhibits COX-1 more than COX-2, while indomethacin is considered a COX-2 inhibitor since its COX-2 ($IC_{50}$)/COX-1 ($IC_{50}$) ratio is 33. Even selective COX-2 inhibitors retain some COX-1 inhibition at therapeutic levels obtained in vivo. Cryer and Feldman, Am J. Med. 104(5):413-21 (1998).

Commercially available NSAIDs which can be used in the methods and compositions of the invention include the traditional NSAIDs diclofenac potassium, diclofenac sodium, diclofenac sodium with misoprostol, diflunisal, etodolac, fenoprofen calcium, flurbiprofen, ibuprofen, indomethacin, ketoprofen, meclofenamate sodium, mefenamic acid, meloxicam, nabumetone, naproxen sodium, piroxicam, tolmetin sodium, the COX-2 inhibitors celecoxib, rofecoxib, and valdecoxib, the acetylated salicylates, such as aspirin, and the non-acetylated salicylates, such as magnesium salicylate, choline salicylate, salsalate, and sodium salicylate.

IV. 5-LOX Inhibitors

Metabolism of arachidonic acid through the lipoxygenase ("LOX") pathway lead to the formation of leukotrienes ("LTs") that are implicated in a range of pathologies. The primary inflammatory enzyme is 5-lipoxygenase ("5-LOX"). The 5-LOX cascade results in the formation of LTB4 and the cysteinyl LTs LTC4, LTD4, and LTE4. LTB4 is a potent stimulator of leukocyte activation. Cysteinyl LTs "may participate in the damage of gastric mucosa by inducing mucosal microvascular injury and gastric vessel vasoconstriction, promoting breakdown of the mucosal barrier and stimulating the secretion of gastric acid, as well as the production of interleukin 1 ("IL1") and proinflammatory cytokines." Martel-Pelletier et al., Ann. Rheumatic Dis 62:501-509 (2003) ("Martel-Pelletier 2003"). Additional lipoxygenases, 12-LOX and 15-LOX, exist that contribute to the formation of anti-inflammatory compounds known as lipoxins, or LXs. Thus, for purposes of reducing inflammation, it is desirable to inhibit 5-LOX without also inhibiting 12-LOX and 15-LOX.

Because of its role in inflammation, a number of inhibitors of 5-LOX have been developed. See, e.g., Julemont et al., Expert Opinion on Therapeutic Patents, 13(1):1-13 (2003) (review of patents directed to 5-LOX inhibitors for 1999-2002). One orally effective inhibitor is REV 5901 [alpha-pentyl-3-(2-quinolinylmethoxy)-benzene-methanol] (see, Van Inwegen et al., Pharmacol Exp Therapeutics 241(1):117-124 (1987)). 5-LOX can also be inhibited by inhibiting the 5-lipoxygenase activating protein ("FLAP") by MK-886. (see, Smirnov et al., Br J Pharmacol 124:572-578 (1998)). This inhibitor, however, induces apoptosis in some cell types and is best used in in vitro studies. Other inhibitors are described in, e.g., U.S. Patent Application No. 20040198768

V. Joint COX/LOX Inhibitors

Because of the inflammatory effects of prostaglandins and leukotrienes, and because blocking the COX pathway has been thought to shuttle arachidonic acid into the LOX pathway, it has been suggested that dual inhibition of both COX-2 and 5-LOX would maximize the inhibition of inflammation. See, e.g., Martel-Pelletier 2003, supra. Several compounds have been developed to block both COX-2 and 5-LOX. One, tepoxalin, blocks COX-1, COX-2, and 5-LOX, and is commercially available as a veterinary pharmaceutical for dogs, under the name Zubrin® (Schering Plough Animal Health Corp., Union, N.J.). Tepoxalin has also been shown to block the COX enzymes and LOX in humans and to be well tolerated. A second inhibitor of COX and 5-LOX, licofelone (Merkle GmbH, Germany), is in Phase III clinical trials as a treatment for osteoarthritis and has shown gastric tolerability superior to naproxen. See, Bias et al., Am J Gastroenterol 99(4):611 (2004). See also, Martel-Pelletier 2003, supra; Tries et al., Inflamm Res 51:135-43 (2002). A number of other dual COX/LOX inhibitors, and especially COX-2/5-LOX inhibitors, have been developed, as exemplified by U.S. Pat. No. 6,753,344 (thiophene substituted hydroxamic acid derivatives), U.S. Pat. No. 6,696,477 (heterocyclo substituted hydroxamic acid derivatives), U.S. Pat. No. 6,677,364 (substituted sulfonylphenylheterocycles), and U.S. Patent Application Nos. 20040248943 (pyrazole substituted hydroxamic acid derivatives), 20040147565 (substituted sulfonylphenylheterocycles), 20030180402 (flavans isolated from the genus Acacia), and 20030176708 (thiophene substituted hydroxamic acid derivatives).

VI. Inhibitors of Soluble Epoxide Hydrolase

Scores of sEH inhibitors are known, of a variety of chemical structures. 1,3 disubstituted ureas, carbamates, and amides (each of which is also referred to herein as a "primary pharmacophore") have been reported as stable and potent inhibitors of sEH. See, U.S. Pat. No. 6,150,415 (the "'415 patent"). In some preferred embodiments, the inhibitors are those described in co-owned PCT Application PCT/US04/10298, published as international publication WO 2004/089296, incorporated herein by reference. The introduction of secondary or tertiary pharmacophores, or both, can increase water solubility and oral availability of sEH inhibitors. In a particularly preferred embodiment, the inhibitor has a disubstituted urea, carbamate, or amide as a primary pharmacophore and has a polyether as a secondary pharmacophore. Derivatives that are metabolically stable are preferred, as they are expected to have greater activity in vivo.

Derivatives in which the primary pharmacophore is covalently bound to both an adamantane and to a 12 carbon chain dodecane are also useful as sEH inhibitors. Selective and competitive inhibition of sEH in vitro by a variety of urea, carbamate, and amide derivatives is taught, for example, by Morisseau et al., Proc. Natl. Acad. Sci. U.S.A, 96:8849-8854 (1999), which provides substantial guidance on designing urea derivatives that inhibit the enzyme.

Derivatives of urea are transition state mimetics that form a preferred group of sEH inhibitors. Within this group, N,N'-dodecyl-cyclohexyl urea (DCU), is preferred as an inhibitor, while N-cyclohexyl-N'-dodecylurea (CDU) is particularly preferred. Some compounds, such as dicyclohexylcarbodiimide (a lipophilic diimide), can decompose to an active urea inhibitor such as DCU. Any particular urea derivative or other compound can be easily tested for its ability to inhibit sEH by standard assays, such as those discussed herein. The production and testing of urea and carbamate derivatives as sEH inhibitors is set forth in detail in, for example, Morisseau et al., Proc Natl Acad Sci (USA) 96:8849-8854 (1999).

N-Adamantyl-N'-dodecyl urea ("ADU") is both metabolically stable and has particularly high activity on sEH. (Both the 1- and the 2-admamantyl ureas have been tested and have about the same high activity as an inhibitor of sEH.) Thus, isomers of adamantyl dodecyl urea are particularly preferred inhibitors. It is further expected that other dodecanoic acid ester derivatives of urea are suitable for use in the methods of the invention. In a preferred embodiment, the inhibitor is 12-(3-adamantane-1-yl-ureido)-dodecanoic acid (AUDA) or an ester thereof. In a particularly preferred form, the inhibitor is AUDA-butyl ester (AUDA-NBE or "AUDA-BE").

U.S. Pat. No. 5,955,496 (the '496 patent) sets forth a number of suitable epoxide hydrolase inhibitors for use in the methods of the invention. One category of inhibitors comprises inhibitors that mimic the substrate for the enzyme. The lipid alkoxides (e.g., the 9-methoxide of stearic acid) are an exemplar of this group of inhibitors. In addition to the inhibitors discussed in the '496 patent, a dozen or more lipid alkoxides have been tested as sEH inhibitors, including the methyl, ethyl, and propyl alkoxides of oleic acid (also known as stearic acid alkoxides), linoleic acid, and arachidonic acid, and all have been found to act as inhibitors of sEH.

In another group of embodiments, the '496 patent sets forth sEH inhibitors that provide alternate substrates for the enzyme that are turned over slowly. Exemplars of this category of inhibitors are phenyl glycidols (e.g., S, S-4-nitrophenylglycidol), and chalcone oxides. The '496 patent notes that suitable chalcone oxides include 4-phenylchalcone oxide and 4-fluourochalcone oxide. The phenyl glycidols and chalcone oxides are believed to form stable acyl enzymes.

Additional inhibitors of sEH suitable for use in the methods of the invention are set forth in the '415 patent and in U.S. Pat. No. 6,531,506 (the '506 patent). Two preferred classes of inhibitors of the invention are compounds of Formulas 1 and 2, as described in the '415 and '506 patents. Means for preparing such compounds and assaying desired compounds for the ability to inhibit epoxide hydrolases are also described. The '506 patent, in particular, teaches scores of inhibitors of Formula 1 and some twenty inhibitors of Formula 2, which were shown to inhibit human sEH at concentrations as low as 0.1 M. Any particular inhibitor can readily be tested to determine whether it will work in the methods of the invention by standard assays, such as that set forth in the Examples, below.

As noted above, chalcone oxides can serve as an alternate substrate for the enzyme. While chalcone oxides have half lives which depend in part on the particular structure, as a group the chalcone oxides tend to have relatively short half lives (a drug's half life is usually defined as the time for the concentration of the drug to drop to half its original value. See, e.g., Thomas, G., MEDICINAL CHEMISTRY: AN INTRODUCTION, John Wiley & Sons Ltd. (West Sussex, England, 2000)). Since the uses of the invention contemplate inhibition of sEH over periods of time which can be measured in days, weeks, or months, chalcone oxides, and other inhibitors which have a half life whose duration is shorter than the practitioner deems desirable, are preferably administered in a manner which provides the agent over a period of time. For example, the inhibitor can be provided in materials that release the inhibitor slowly. Methods of administration that permit high local concentrations of an inhibitor over a period of time are known, and are not limited to use with inhibitors which have short half lives although, for inhibitors with a relatively short half life, they are a preferred method of administration.

In addition to the compounds in Formula 1 of the '506 patent, which interact with the enzyme in a reversible fashion based on the inhibitor mimicking an enzyme-substrate transition state or reaction intermediate, one can have compounds that are irreversible inhibitors of the enzyme. The active structures such as those in the Tables or Formula 1 of the '506 patent can direct the inhibitor to the enzyme where a reactive functionality in the enzyme catalytic site can form a covalent bond with the inhibitor. One group of molecules which could interact like this would have a leaving group such as a halogen or tosylate which could be attacked in an SN2 manner with a lysine or histidine. Alternatively, the reactive functionality could be an epoxide or Michael acceptor such as an unsaturated ester, aldehyde, ketone, ester, or nitrile.

Further, in addition to the Formula 1 compounds, active derivatives can be designed for practicing the invention. For example, dicyclohexyl thio urea can be oxidized to dicyclohexylcarbodiimide which, with enzyme or aqueous acid (physiological saline), will form an active dicyclohexylurea. Alternatively, the acidic protons on carbamates or ureas can be replaced with a variety of substituents which, upon oxidation, hydrolysis or attack by a nucleophile such as glutathione, will yield the corresponding parent structure. These materials are known as prodrugs or protoxins (Gilman et al., THE PHARMACOLOGICAL BASIS OF THERAPEUTICS, 7th Edition, MacMillan Publishing Company, New York, p. 16 (1985)) Esters, for example, are common prodrugs which are released to give the corresponding alcohols and acids enzymatically (Yoshigae et al., Chirality, 9:661-666 (1997)). The drugs and prodrugs can be chiral for greater specificity. These derivatives have been extensively used in medicinal and agricultural chemistry to alter the pharmacological properties of the compounds such as enhancing water solubility, improving formulation chemistry, altering tissue targeting, altering volume of distribution, and altering penetration. They also have been used to alter toxicology profiles.

There are many prodrugs possible, but replacement of one or both of the two active hydrogens in the ureas described here or the single active hydrogen present in carbamates is particularly attractive. Such derivatives have been extensively described by Fukuto and associates. These derivatives have been extensively described and are commonly used in agricultural and medicinal chemistry to alter the pharmacological properties of the compounds. (Black et al., J Agric Food Chem, 21(5):747-751 (1973); Fahmy et al, J Agric Food Chem, 26(3):550-556 (1978); Jojima et al., J Agric Food Chem, 31(3):613-620 (1983); and Fahmy et al., J Agric Food Chem, 29(3):567-572 (1981).)

Such active proinhibitor derivatives are within the scope of the present invention, and the just-cited references are incorporated herein by reference. Without being bound by theory, it is believed that suitable inhibitors of the invention mimic the enzyme transition state so that there is a stable interaction with the enzyme catalytic site. The inhibitors appear to form hydrogen bonds with the nucleophilic carboxylic acid and a polarizing tyrosine of the catalytic site.

In some embodiments, sEH inhibition can include the reduction of the amount of sEH. As used herein, therefore, sEH inhibitors can therefore encompass nucleic acids that inhibit expression of a gene encoding sEH. Many methods of reducing the expression of genes, such as reduction of transcription and siRNA, are known, and are discussed in more detail below.

Preferably, the inhibitor inhibits sEH without also significantly inhibiting microsomal epoxide hydrolase ("mEH"). Preferably, at concentrations of 500 M, the inhibitor inhibits sEH activity by at least 50% while not inhibiting mEH activity by more than 10%. Preferred compounds have an IC50 (inhibition potency or, by definition, the concentration of inhibitor which reduces enzyme activity by 50%) of less than about 500 M. Inhibitors with IC50s of less than 500 M are preferred, with IC50s of less than 100 M being more preferred and IC50s of 50 M, 40 M, 30 M, 25 M, 20 M, 15 M, 10 M, 5 M, 3 M, 2 M, 1 M or even less being the more preferred as the IC50 decreases. Assays for determining EH activity are known in the art and described elsewhere herein.

VII. EETs and Epoxides of EPA and DHA

In some embodiments of the invention, one or more EETs, or epoxide or epoxides of DHA or of EPA, or both, are administered concurrently with, or after the administration, of an sEH inhibitor. Optionally, the EET or EETs or epoxides of DHA or of EPA, or both, are embedded or otherwise placed in a material that releases the EET, or epoxides of DHA or of EPA, or both, over time. Materials suitable for promoting the slow release of compositions such as EETs and epoxides of DHA and EPA are known in the art.

Conveniently, the EET or EETs or epoxide or epoxides of DHA or of EPA, or both, can be administered orally. Since these epoxides are subject to degradation under acidic conditions, epoxides intended for oral administration can be coated with a coating resistant to dissolving under acidic conditions, but which dissolve under the mildly basic conditions present in the intestines. Suitable coatings, commonly known as "enteric coatings" are widely used for products such as aspirin which cause gastric distress or which would undergo degradation upon exposure to gastric acid. By using coatings with an appropriate dissolution profile, the coated substance can be released in a chosen section of the intestinal tract. For example, a substance to be released in the colon is coated with a substance that dissolves at pH 6.5-7, while substances to be released in the duodenum can be coated with a coating that dissolves at pH values over 5.5. Such coatings are commercially available from, for example, Rohm Specialty Acrylics (Rohm America LLC, Piscataway, N.J.) under the trade name "Eudragit®". The choice of the particular enteric coating is not critical to the practice of the invention.

Preferred EETs include 14,15-EET, 8,9-EET and 11,12-EET in that order of preference. Purified sEH selected 8S,9R- and 14R,15S-EET; accordingly these EETs are particularly preferred. 8,9-EET, 11,12-EET, and 14R,15S-EET are commercially available from, for example, Sigma-Aldrich (catalog nos. E5516, E5641, and E5766, respectively, Sigma-Aldrich Corp., St. Louis, Mo.). Any of the epoxides of EPA or DHA can be used.

VIII. Assays for Epoxide Hydrolase Activity

Any of a number of standard assays for determining epoxide hydrolase activity can be used to determine inhibition of sEH. For example, suitable assays are described in Gill, et al., Anal Biochem 131, 273-282 (1983); and Borhan, et al., Analytical Biochemistry 231, 188-200 (1995)). Suitable in vitro assays are described in Zeldin et al., J Biol. Chem. 268:6402-6407 (1993). Suitable in vivo assays are described in Zeldin et al., Arch Biochem Biophys 330:87-96 (1996). Assays for epoxide hydrolase using both putative natural substrates and surrogate substrates have been reviewed (see, Hammock, et al. In: METHODS IN ENZYMOLOGY, Volume III, Steroids and Isoprenoids, Part B, (Law, J. H. and H. C. Rilling, eds. 1985), Academic Press, Orlando, Fla., pp. 303-311 and Wixtrom et al., In: BIOCHEMICAL PHARMACOLOGY AND TOXICOLOGY, Vol. 1: Methodological Aspects of Drug Metabolizing Enzymes, (Zakim, D. and D. A. Vessey, eds. 1985), John Wiley & Sons, Inc., New York, pp. 1-93. Several spectral based assays exist based on the reactivity or tendency of the resulting diol product to hydrogen bond (see, e.g., Wixtrom, supra, Hammock. Anal. Biochem. 174:291-299 (1985) and Dietze, et al. Anal. Biochem. 216:176-187 (1994)).

The enzyme also can be detected based on the binding of specific ligands to the catalytic site which either immobilize the enzyme or label it with a probe such as dansyl, fluoracein, luciferase, green fluorescent protein or other reagent. The enzyme can be assayed by its hydration of EETs, its hydrolysis of an epoxide to give a colored product as described by Dietze et al., 1994, supra, or its hydrolysis of a radioactive surrogate substrate (Borhan et al., 1995, supra). The enzyme also can be detected based on the generation of fluorescent products following the hydrolysis of the epoxide. Numerous method of epoxide hydrolase detection have been described (see, e.g., Wixtrom, supra).

The assays are normally carried out with a recombinant enzyme following affinity purification. They can be carried out in crude tissue homogenates, cell culture or even in vivo, as known in the art and described in the references cited above.

IX. Other Means of inhibiting sEH Activity

Other means of inhibiting sEH activity or gene expression can also be used in the compositions and methods of the invention. For example, a nucleic acid molecule complementary to at least a portion of the human sEH gene can be used to inhibit sEH gene expression. Means for inhibiting gene expression using, for example, short interfering RNA (siRNA) and microRNA (miRNA), are known. "RNA interference", a form of post-transcriptional gene silencing ("PTGS"), describes effects that result from the introduction of double-stranded RNA into cells (reviewed in Fire, A. Trends Genet 15:358-363 (1999); Sharp, P. Genes Dev 13:139-141 (1999); Hunter, C. Curr Biol 9:R440-R442 (1999); Baulcombe. D. Curr Biol 9:R599-R601 (1999); Vaucheret et al. Plant J 16: 651-659 (1998)). RNA interference, commonly referred to as RNAi, offers a way of specifically inactivating a cloned gene.

The active agent in RNAi is a long double-stranded (antiparallel duplex) RNA, with one of the strands corresponding or complementary to the RNA which is to be inhibited. The inhibited RNA is the target RNA. The long double stranded RNA is chopped into smaller duplexes of approximately 20 to 25 nucleotide pairs, after which the mechanism by which the smaller RNAs inhibit expression of the target is largely unknown at this time. While RNAi was shown initially to work well in lower eukaryotes, for mammalian cells, it was thought that RNAi might be suitable only for studies on the oocyte and the preimplantation embryo. In mammalian cells other than these, however, longer RNA duplexes provoked a response known as "sequence non-specific RNA interference," characterized by the non-specific inhibition of protein synthesis.

Further studies showed this effect to be induced by dsRNA of greater than about 30 base pairs, apparently due to an interferon response. It is thought that dsRNA of greater than about 30 base pairs binds and activates the protein PKR and 2',5'-oligonucleotide synthetase (2',5'-AS). Activated PKR stalls translation by phosphorylation of the translation initiation factors eIF2α, and activated 2',5'-AS causes mRNA degradation by 2',5'-oligonucleotide-activated ribonuclease L. These responses are intrinsically sequence-nonspecific to the inducing dsRNA; they also frequently result in apoptosis, or cell death. Thus, most somatic mammalian cells undergo apoptosis when exposed to the concentrations of dsRNA that induce RNAi in lower eukaryotic cells.

More recently, it was shown that RNAi would work in human cells if the RNA strands were provided as pre-sized duplexes of about 19 nucleotide pairs, and RNAi worked particularly well with small unpaired 3' extensions on the end of each strand (Elbashir et al. Nature 411: 494-498 (2001)). In this report, "short interfering RNA" (siRNA, also referred to as small interfering RNA) were applied to cultured cells by transfection in oligofectamine micelles. These RNA duplexes were too short to elicit sequence-nonspecific responses like apoptosis, yet they efficiently initiated RNAi. Many laboratories then tested the use of siRNA to knock out target genes in mammalian cells. The results demonstrated that siRNA works quite well in most instances.

For purposes of reducing the activity of sEH, siRNAs to the gene encoding sEH can be specifically designed using computer programs. The cloning, sequence, and accession numbers of the human sEH sequence are set forth in Beetham et al., Arch. Biochem. Biophys. 305(1):197-201 (1993). The amino acid sequence of human sEH is also set forth as SEQ ID NO:2 of U.S. Pat. No. 5,445,956; nucleotides 42-1703 of SEQ ID NO:1 of the '956 patent are the nucleic acid sequence encoding the amino acid sequence.

A program, siDESIGN from Dharmacon, Inc. (Lafayette, Colo.), permits predicting siRNAs for any nucleic acid sequence, and is available on the World Wide Web at dharmacon.com. Programs for designing siRNAs are also available from others, including Genscript (available on the Web at genscript.com/ssl-bin/ap p/rnai) and, to academic and non-profit researchers, from the Whitehead Institute for Biomedical Research on the internet by entering "http://" followed by "jura.wi.mit.edu/pubint/http://iona.wi.mit.edu/siRNAext/."

For example, using the program available from the Whitehead Institute, the following sEH target sequences and siRNA sequences can be generated:

```
1) Target:          CAGTGTTCATTGGCCATGACTGG       (SEQ ID NO: 3)
   Sense-siRNA:     5' - GUGUUCAUUGGCCAUGACUTT- 3' (SEQ ID NO: 4)
   Antisense-siRNA: 5' - AGUCAUGGCCAAUGAACACTT- 3' (SEQ ID NO: 5)

2) Target:          GAAAGGCTATGGAGAGTCATCTG       (SEQ ID NO: 6)
   Sense-siRNA:     5' - AAGGCUAUGGAGAGUCAUCTT-3'  (SEQ ID NO: 7)
   Antisense-siRNA: 5' - GAUGACUCUCCAUAGCCUUTT-3'  (SEQ ID NO: 8)

3) Target:          AAAGGCTATGGAGAGTCATCTGC       (SEQ ID NO: 9)
   Sense-siRNA:     5' - AGGCUAUGGAGAGUCAUCUTT- 3' (SEQ ID NO: 10)
   Antisense-siRNA: 5' - AGAUGACUCUCCAUAGCCUTT- 3' (SEQ ID NO: 11)

4) Target:          CAAGCAGTGTTATTGGCCATGA        (SEQ ID NO: 12)
   Sense-siRNA:     5' - AGCAGUGUUCAUUGGCCAUTT- 3' (SEQ ID NO: 13)
   Antisense-siRNA: 5' - AUGGCCAAUGAACACUGCUTT- 3' (SEQ ID NO: 14)

5) Target:          CAGCACATGGAGGACTGGATTCC       (SEQ ID NO: 15)
   Sense-siRNA:     5' - GCACAUGGAGGACUGGAUUTT- 3' (SEQ ID NO: 16)
   Antisense-siRNA: 5' - AAUCCAGUCCUCCAUGUGCTT- 3' (SEQ ID NO: 17)
```

Alternatively, siRNA can be generated using kits which generate siRNA from the gene. For example, the "Dicer siRNA Generation" kit (catalog number T510001, Gene Therapy Systems, Inc., San Diego, Calif.) uses the recombinant human enzyme "dicer" in vitro to cleave long double stranded RNA into 22 bp siRNAs. By having a mixture of siRNAs, the kit permits a high degree of success in generating siRNAs that will reduce expression of the target gene. Similarly, the Silencer™ siRNA Cocktail Kit (RNase III) (catalog no. 1625, Ambion, Inc., Austin, Tex.) generates a mixture of siRNAs from dsRNA using RNase III instead of dicer. Like dicer, RNase III cleaves dsRNA into 12-30 bp dsRNA fragments with 2 to 3 nucleotide 3' overhangs, and 5'-phosphate and 3'-hydroxyl termini. According to the manufacturer, dsRNA is produced using T7 RNA polymerase, and reaction and purification components included in the kit. The dsRNA is then digested by RNase III to create a population of siRNAs. The kit includes reagents to synthesize long dsRNAs by in vitro transcription and to digest those dsRNAs into siRNA-like molecules using RNase III. The manufacturer indicates that the user need only supply a DNA template with opposing T7 phage polymerase promoters or two separate templates with promoters on opposite ends of the region to be transcribed.

The siRNAs can also be expressed from vectors. Typically, such vectors are administered in conjunction with a second vector encoding the corresponding complementary strand. Once expressed, the two strands anneal to each other and form the functional double stranded siRNA. One exemplar vector suitable for use in the invention is pSuper, available from OligoEngine, Inc. (Seattle, Wash.). In some embodiments, the vector contains two promoters, one positioned downstream of the first and in antiparallel orientation. The first promoter is transcribed in one direction, and the second in the direction antiparallel to the first, resulting in expression of the complementary strands. In yet another set of embodiments, the promoter is followed by a first segment encoding the first strand, and a second segment encoding the second strand. The second strand is complementary to the palindrome of the first strand. Between the first and the second strands is a section of RNA serving as a linker (sometimes called a "spacer") to permit the second strand to bend around and anneal to the first strand, in a configuration known as a "hairpin."

The formation of hairpin RNAs, including use of linker sections, is well known in the art. Typically, an siRNA expression cassette is employed, using a Polymerase III promoter such as human U6, mouse U6, or human H1. The coding sequence is typically a 19-nucleotide sense siRNA sequence linked to its reverse complementary antisense siRNA sequence by a short spacer. Nine-nucleotide spacers are typical, although other spacers can be designed. For example, the Ambion website indicates that its scientists have had success with the spacer TTCAAGAGA (SEQ ID NO:18). Further, 5-6 T's are often added to the 3' end of the oligonucleotide to serve as a termination site for Polymerase III. See also, Yu et al., Mol Ther 7(2):228-36 (2003); Matsukura et al., Nucleic Acids Res 31(15):e77 (2003).

As an example, the siRNA targets identified above can be targeted by hairpin siRNA as follows. And if you would like to attack the same targets by short hairpin RNAs, produced by a vector (permanent RNAi effect) you would put sense and antisense strand in a row with a loop forming sequence in between and suitable sequences for an adequate expression vector to both ends of the sequence. The ends of course depend on the cutting sites of the vector. The following are non-limiting examples of hairpin sequences that can be cloned into the pSuper vector:

```
1) Target:          CAGTGTTCATTGGCCATGACTGG                                            (SEQ ID NO: 19)
   Sense strand:    5'-GATCCCCGTGTTCATTGGCCATGACTTTCAAGAGAAGTCATGGCCAATGAACACTTTTT-3'   (SEQ ID NO: 20)
   Antisense strand:5'-AGCTAAAAAGTGTTCATTGGCCATGACTTCTCTTGAAAGTCATGGCCAATGAACACGGG-3'   (SEQ ID NO: 21)

2) Target:          GAAAGGCTATGGAGAGTCATCTG                                            (SEQ ID NO: 22)
   Sense strand:    5'-GATCCCCAAGGCTATGGAGAGTCATCTTCAAGAGAGATGACTCTCCATAGCCTTTTTT-3'    (SEQ ID NO: 23)
   Antisense strand:5'-AGCTAAAAAAGGCTATGGAGAGTCATCTCTCTTGAAGATGACTCTCCATAGCCTTGGG-3'    (SEQ ID NO: 24)

3) Target:          AAAGGCTATGGAGAGTCATCTGC                                            (SEQ ID NO: 25)
   Sense strand:    5'-GATCCCCAGGCTATGGAGAGTCATCTTTCAAGAGAAGATGACTCTCCATAGCCTTTTTT-3'   (SEQ ID NO: 26)
   Antisense strand:5'-AGCTAAAAAAGGCTATGGAGAGTCATCATCTCTTGAAAGATGACTCTCCATAGCCTGGG-3'   (SEQ ID NO: 27)
```

```
4)  Target:           CAAGCAGTGTTCATTGGCCATGA                                             (SEQ ID NO: 28)
    Sense strand:     5'-GATCCCCAGCAGTGTTCATTGGCCATTTCAAGAGAATGGCCAATGAACACTGCTTTTTT-3'    (SEQ ID NO: 29)
    Antisense strand: 5'-AGCTAAAAAAGCAGTGTTCATTGGCCATTCTCTTGAAATGGCCAATGAACACTGCTGGG-3'    (SEQ ID NO: 30)

5)  Target:           GAGCACATGGAGGACTGGATTCC                                              (SEQ ID NO: 31)
    Sense strand:     5'-GATCCCCGCACATGGAGGACTGGATTTTCAAGAGAAATCCAGTCCTCCATGTGCTTTTT-3'    (SEQ ID NO: 32)
    Antisense strand: 5'-AGCTAAAAAGCACATGGAGGACTGGATTTCTCTTGAAAATCCAGTCCTCCATGTGCGGG-3'    (SEQ ID NO: 33)
```

Another method of inhibiting expression of sEH is the use of miRNA. MicroRNAs (miRNAs) interact with target mRNAs at specific sites to induce cleavage of the message or inhibit translation, and may impact the expression of as much as 10% of human proteins. See, e.g., John, et al., PLOS Biol, vol. 2, issue 11 (November 2004), available on the Web by entering plosbiology.org/plosonline/?request=get-document&doi=10.1371%2F journal.pbio.0020363. The open source program miRanda (Enright et al., Genome Biology (2003) 5;R1), available on the web at microma.org/miranda.html, is an algorithm for finding genomic targets for microRNAs developed by the Computational Biology Center of Memorial Sloan-Kettering Cancer Center.

In addition to siRNAs and miRNA, other nucleic acid molecules for inhibiting gene expression, such as antisense molecules, ribozymes, and the like, are well known to those of skill in the art. The nucleic acid molecule can be a DNA probe, a riboprobe, a peptide nucleic acid probe, a phosphorothioate probe, or a 2'-O methyl probe.

With respect to antisense molecules and the targeting portion of ribozymes, to assure specific hybridization, the antisense sequence is generally complementary to the target sequence. In certain embodiments, the antisense sequence is exactly complementary to the target sequence. The antisense polynucleotides may also include, however, nucleotide substitutions, additions, deletions, transitions, transpositions, or modifications, or other nucleic acid sequences or non-nucleic acid moieties so long as specific binding to the relevant target sequence corresponding to the sEH gene is retained as a functional property of the polynucleotide. In one embodiment, the antisense molecules form a triple helix-containing, or "triplex" nucleic acid. Triple helix formation results in inhibition of gene expression by, for example, preventing transcription of the target gene (see, e.g., Cheng et al., 1988, J. Biol. Chem. 263:15110; Ferrin and Camerini-Otero, 1991, Science 354:1494; Ramdas et al., 1989, J. Biol. Chem. 264: 17395; Strobel et al., 1991, Science 254:1639; and Rigas et al., 1986, Proc. Natl. Acad. Sci. U.S.A. 83:9591)

Antisense molecules can be designed by methods known in the art. For example, Integrated DNA Technologies (Coralville, Iowa) makes available a program on the internet which can be found by entering http://, followed by biotools.idtdna.com/antisense/AntiSense.aspx, which will provide appropriate antisense sequences for nucleic acid sequences up to 10,000 nucleotides in length. Using this program with the sEH gene provides the following exemplar sequences:

```
1) UGUCCAGUGCCCACAGUCCU    (SEQ ID NO: 34)
2) UUCCCACCUGACACGACUCU    (SEQ ID NO: 35)
3) GUUCAGCCUCAGCCACUCCU    (SEQ ID NO: 36)
4) AGUCCUCCCGCUUCACAGA     (SEQ ID NO: 37)
5) GCCCACUUCCAGUUCCUUUCC   (SEQ ID NO: 38)
```

In another embodiment, ribozymes can be designed to cleave the in RNA at a desired position. (See, e.g., Cech, 1995, Biotechnology 13:323; and Edgington, 1992, Biotechnology 10:256 and Hu et al., PCT Publication WO 94/03596).

The antisense nucleic acids (DNA, RNA, modified, analogues, and the like) can be made using any suitable method for producing a nucleic acid, such as the chemical synthesis and recombinant methods disclosed herein and known to one of skill in the art. In one embodiment, for example, antisense RNA molecules of the invention may be prepared by de novo chemical synthesis or by cloning. For example, an antisense RNA can be made by inserting (ligating) a sEH gene sequence in reverse orientation operably linked to a promoter in a vector (e.g., plasmid). Provided that the promoter and, preferably termination and polyadenylation signals, are properly positioned, the strand of the inserted sequence corresponding to the noncoding strand will be transcribed and act as an antisense oligonucleotide of the invention.

It will be appreciated that the oligonucleotides can be made using nonstandard bases (e.g., other than adenine, cytidine, guanine, thymine, and uridine) or nonstandard backbone structures to provides desirable properties (e.g., increased nuclease-resistance, tighter-binding, stability or a desired Tm). Techniques for rendering oligonucleotides nuclease-resistant include those described in PCT Publication WO 94/12633. A wide variety of useful modified oligonucleotides may be produced, including oligonucleotides having a peptide-nucleic acid (PNA) backbone (Nielsen et al., Science 254:1497 (1991)) or incorporating 2'-O-methyl ribonucleotides, phosphorothioate nucleotides, methyl phosphonate nucleotides, phosphotriester nucleotides, phosphorothioate nucleotides, phosphoramidates.

Proteins have been described that have the ability to translocate desired nucleic acids across a cell membrane. Typically, such proteins have amphiphilic or hydrophobic subsequences that have the ability to act as membrane-translocating carriers. For example, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, Current Opinion in Neurobiology 6:629-634 (1996)). Another subsequence, the h (hydrophobic) domain of signal peptides, was found to have similar cell membrane translocation characteristics (see, e.g., Lin et al., J. Biol. Chem. 270:14255-14258 (1995)). Such subsequences can be used to translocate oligonucleotides across a cell membrane. Oligonucleotides can be conveniently derivatized with such sequences. For example, a linker can be used to link the oligonucleotides and the translocation sequence. Any suitable linker can be used, e.g., a peptide linker or any other suitable chemical linker.

X. Therapeutic Administration

In the compositions of the invention, a COX-1, COX-2, or LOX inhibitor is combined with a sEHI. Optionally, the compositions further comprise one or more EETs or an epoxide of EPA, of DHA, or one or more epoxides of both. In some embodiments, the composition is of an epoxide or EPA, of DHA, or epoxides of both, and an sEHI. The compositions of the invention can be prepared and administered in a wide variety of oral, parenteral and topical dosage forms. In preferred forms, compositions for use in the methods of the present invention can be administered orally, by injection, that is, intravenously, intramuscularly, intracutaneously, subcutaneously, intraduodenally, or intraperitoneally. The compositions can also be administered by inhalation, for example, intranasally. Additionally, the compositions can be administered transdermally. Accordingly, in some embodiments, the methods of the invention permit administration of compositions comprising a pharmaceutically acceptable carrier or excipient, an inhibitor of COX-1, of COX-2, or of both, or an inhibitor of a LOX, a selected sEHI inhibitor or a pharmaceutically acceptable salt of the inhibitor and, optionally, one or more EETs or epoxides of EPA or of DHA, or of both. In some embodiments, the methods of the invention comprise administration of an sEHI and one or more epoxides of EPA or of DHA, or of both.

For preparing the pharmaceutical compositions, the pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired. The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution. Transdermal administration can be performed using suitable carriers. If desired, apparatuses designed to facilitate transdermal delivery can be employed. Suitable carriers and apparatuses are well known in the art, as exemplified by U.S. Pat. Nos. 6,635,274, 6,623,457, 6,562,004, and 6,274,166.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active components in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention.

A therapeutically effective amount of one or more of the following: an sEH inhibitor, an EET, an EpDPE, or an EpETE, is employed to act as an analgesic alone or in combination with inhibitors of COX-1 or of -2, or both, or of a LOX enzyme. The dosage of the specific compounds depends on many factors that are well known to those skilled in the art. They include for example, the route of administration and the potency of the particular compound. An exemplary dose is from about 0.001 µM/kg to about 100 mg/kg body weight of the mammal.

EETs, EpDPEs, or EpETEs are unstable, and can be converted to the corresponding diols, in acidic conditions, such as those in the stomach. To avoid this, EETs, EpDPEs, or EpETEs can be administered intravenously or by injection. EETs, EpDPEs, or EpETEs intended for oral administration can be encapsulated in a coating that protects the compounds during passage through the stomach. For example, the EETs, EpDPEs, or EpETEs can be provided with a so-called "enteric" coating, such as those used for some brands of aspirin, or embedded in a formulation. Such enteric coatings and formulations are well known in the art. In some formulations, the compositions of the invention are embedded in a slow-release formulation to facilitate administration of the agents over time.

It will be appreciated that the sEHIs and, optionally, the EETs, EpDPEs, or EpETEs, do not need to be combined with the COX-1 inhibitor, COX-2 inhibitor, LOX inhibitor, or COX/LOX inhibitor. They can instead be administered separately. If the sEHIs are administered separately (with or without EETs, EpDPEs, or EpETEs), they should be administered shortly before or concurrently with administration of the COX-1 inhibitor, COX-2 inhibitor, LOX inhibitor, or COX/LOX inhibitor. If the sEHI is administered after administration of the COX-1 inhibitor, COX-2 inhibitor, LOX inhibitor, or COX/LOX inhibitor, it should be administered as soon as possible after administration of the COX-1 inhibitor, COX-2 inhibitor, LOX inhibitor, or COX/LOX inhibitor to maximize the synergy with the other inhibitor. Administration of the sEHI will still be beneficial even if it follows the COX-1 inhibitor, COX-2 inhibitor, LOX inhibitor, or COX/LOX inhibitor by some time, however, so long as amounts of the COX-1 inhibitor, COX-2 inhibitor, LOX inhibitor, or COX/LOX inhibitor sufficient to inhibit the respective enzyme are still present.

It is understood that, like all drugs, sEHIs have half lives defined by the rate at which they are metabolized by or excreted from the body, and that the sEHIs will have a period following administration during which they will be present in amounts sufficient to be effective. If EETs, EpDPEs, or EpETEs are administered after the sEHI is administered, therefore, it is desirable that the EETs, EpDPEs, or EpETEs be administered during the period during which the sEHI will be present in amounts to be effective in delaying hydrolysis of the EETs, EpDPEs, or EpETEs. Typically, the EETs, EpDPEs, or EpETEs will be administered within 48 hours of administering an sEH inhibitor. Preferably, the EETs, EpDPEs, or EpETEs are administered within 24 hours of the sEHI, and even more preferably within 12 hours. In increasing order of desirability, the EETs, EpDPEs, or EpETEs are administered within 10, 8, 6, 4, 2, hours, 1 hour, or one half hour after administration of the inhibitor. Most preferably, the EETs, EpDPEs, or EpETEs are administered concurrently with the sEHI.

EXAMPLES

Example 1

Figure 2:
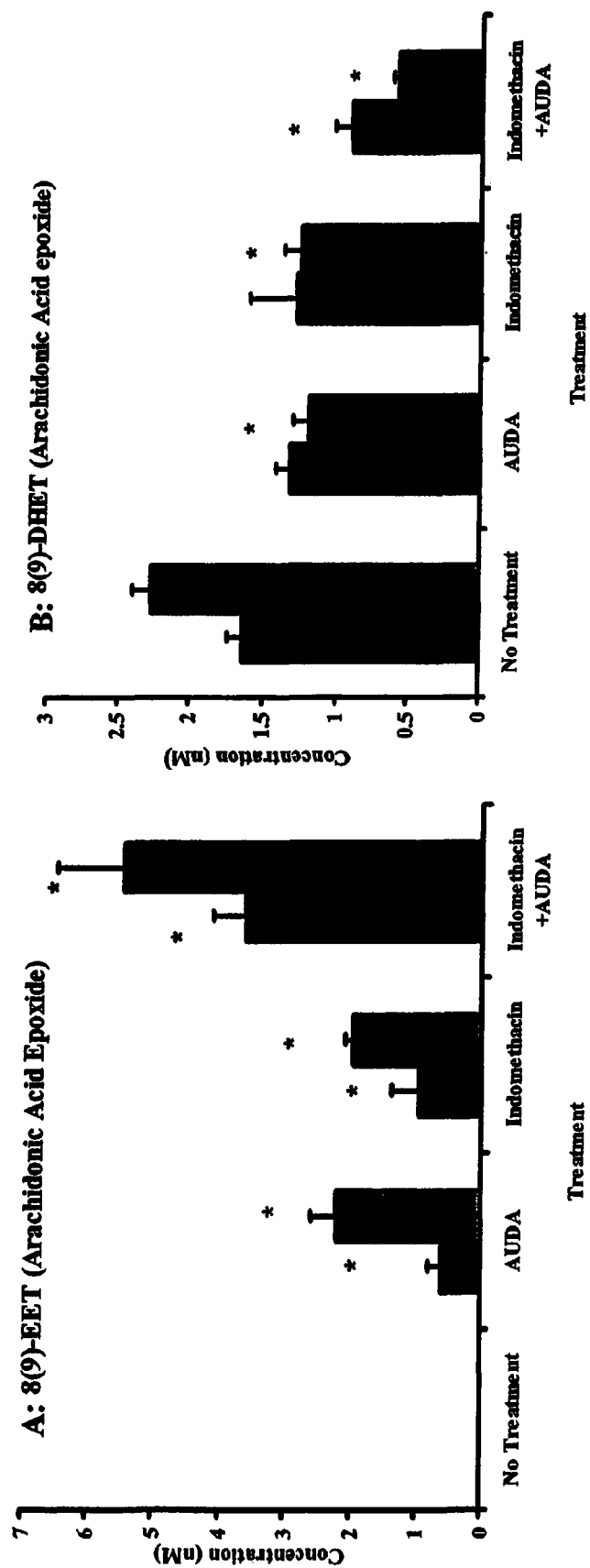
FIGS. 2A and 2B show the levels of 8,9 EETs and 8,9 DHETs, respectively, in mice injected with sterile saline alone (■) or sterile saline with lipopolysaccaride ("LPS") (□). Bars correspond to mean concentration plus or minus standard deviation. N=4 mice for each bar. Mice were treated with the COX-1 and -2 inhibitor indomethacin, or with 12-(3-adamantane-1-yl-ureido)-dodecanoic acid butyl ester ("AUBA-BE"), or with both indomethacin and AUDA-BE.

This Example sets forth the materials and methods used in the studies whose results are set forth in FIGS. 2a and 2b.

Animal Experiments

Male, 7- to 8-week-old C57BL/6 mice (Charles River, Wilmington, Mass.) weighing between 22 and 28 g were used in the inflammation experiments. The mice were acclimated for 5 days prior to experimentation. They were housed in groups of four per cage, in a controlled environment in American Association for Laboratory Animal Care-accredited facilities and were fed mouse chow ad libitum.

The mice were administered lipopolysaccharide ("LPS") to induce inflammatory responses. Saline was used as a carrier for the LPS. The sEH inhibitor used in the studies was 12-(3-adamantane-1-yl-ureido)-dodecanoic acid butyl ester (AUDA-BE). Because AUDA-nBE takes some time to reach physiologically effective levels in the body, mice to which AUDA-BE was to be administered were given the AUDA-BE prior to exposure to LPS.

The mice were divided into groups and the following protocols followed:

(a) Four mice were administered oleic oil (125 µL) (vehicle) subcutaneously ("sc") 24 hrs prior to LPS (10 mg/kg) ip exposure. Immediately following the LPS exposure, another dose of the oleic oil was administered.

(b) Four mice were administered AUDA-BE (20 mg/kg) sc hrs prior to LPS (10 mg/kg) ip exposure. Immediately following the LPS exposure, the mice were administered another dose of the AUDA-BE (20 mg/kg) sc.

(c) Four mice were administered olive oil sub-Q 24 hrs prior to LPS (10 mg/kg) ip exposure. Immediately following the LPS exposure a dose of indomethacin (100 mg/kg) sc.

(d) Four mice were administered AUDA-BE (20 mg/kg) sub-Q 24 hrs prior to LPS (10 mg/kg, i.p.) exposure. Immediately following the LPS exposure another dose of the AUDA-BE (20 mg/kg) sc, and indomethacin (100 mg/kg) sc.

(e) Additional control animals were dosed with AUDA-BE, and or indomethacin, or oleic oil without administering LPS.

Twenty-four hours after LPS administration the mice were given an overdose of pentobarbital by intraperitoneal injection and blood was collected via cardiac puncture with an EDTA rinsed syringe. The plasma was immediately separated and a combination of triphenylphosphine (TPP) and butylated hydroxytoluene (BHT) 0.2% w/w was added. All samples were stored at −80° C. until analysis.

Oxylipin Sample Analysis

Solid-Phase Extraction of Rodent Biological Samples

Serum aliquots (250 µL) were spiked with 26.7 nM of 6-keto PGF1a-d8, 10(11)-EpHep, and 10,11-DiHN and diluted 1:1 v/v with 2.5 mM phosphoric acid immediately before solid-phase extraction (SPE). Sixty mg Oasis®-HLB SPE cartridges (Waters Corporation, Milford, Mass.) were preconditioned with 2 mL of methanol and 2 mL of 2.5 mM phosphoric acid-10% methanol (pH 3.8). After sample loading, cartridges were washed with 2 mL of 2.5 mM phosphoric acid-10% methanol (pH 3.8) and analytes were eluted in 2 mL of ethyl acetate. The ethyl acetate was evaporated under nitrogen gas and the residue was resuspended in 100 µL of methanol containing 26.7 nM of the internal standards (PHAU and CUDA). The samples where then vortexed for 5 minutes and transferred to autosample vials and stored at −80° C. until analysis. Epoxide hydrolysis is routinely <3% using this procedure.

HPLC Separation

Samples were held at 10° C. during analysis and analytes were separated on a Waters Corporation 2790 separation module equipped with a 2.0×150 nm, 5 µm Luna® C18(2) column (Phenomenex Inc., Torrance, Calif.) held at 40° C. using a solvent flow of 350 µL/min. The column was equilibrated with 15% Solvent A (water with 0.1% glacial acetic acid) and 85% Solvent B (88:12 acetonitrile:methanol v/v with 0.1% glacial acetic acid). The initial solvent conditions were held for 30 seconds post injection of a 110 L sample aliquot. Solvent B is then increased to 30% at 2 minutes, 55% at 8 minutes, and 75% at 28 minutes, followed by washing with 100% organic for 5 minutes and returning the system to the initial conditions.

Electrospray and Tandem Mass Spectrometry

Oxylipins were quantified using a Quattro Ultima tandem-quadrupole mass spectrometer (Micromass® division of Waters Corporation) equipped with an electrospray ionization source operated in negative ion mode (capillary voltage: −3.2 kV, cone gas: 125 L/h; desolvation gas: 650 L/h; source temperature: 100° C.; desolvation temperature: 400°; photo multiplier voltage: 650). Optimal cone and collision voltages were established experimentally using argon as the collision gas ($2.3 \times 10^{-3}$ Torr). The mass spectrometer was operated in multi-reaction monitoring (MRM) mode with selected fragment ions being detected in the third quadrupole. Ion dwell times were calculated based on the number of analytes in each MRM and the inter-channel delay to ensure a minimum of 8 scans across the chromatographic peak of any given analyte.

Example 2

This Example discusses the results of the studies conducted using the materials and methods discussed in the previous Example.

FIGS. 2A and 2B show the levels of 8,9 EET and 8,9 DHET, respectively, in mice injected with sterile saline alone or with sterile saline and lipopolysaccharide ("LPS"). As described in Example 1, groups of mice were treated with the COX-1 and -2 inhibitor indomethacin, or with AUDA butyl ester (AUBA-BE), or with both indomethacin and AUDA-BE.

Referring to FIG. 2A, as shown on the far left of the Figure, mice that were not treated with either AUDA-BE or indomethacin showed no detectable levels of 8,9 EET. The results for the three groups of mice represented in the rest of the figure show two bars, one black and one gray. The black bar in each group represents the concentration of 8,9 EET seen in mice that received the treatment (AUDA-BE, indomethacin, or both, as stated on the axis), but which were not also exposed to the inflammatory agent LPS. The gray bars show the concentration of 8,9 EET for mice with the same treatment as the mice in the corresponding black bar, but to which LPS has also been administered. Examination of the graphs reveals that the concentration of 8,9 EET is markedly increased in the mice treated with both the COX-1 and -2 inhibitor indomethacin and with the sEHI AUDA-BE compared to either agent alone. Since EETs are considered to be anti-inflammatory, this indicates that the two agents together show synergism.

FIG. 2B is a corresponding set of graphs showing the concentrations of 8,9 dihydroxyeicosantrienoic acid ("DHET"), which is the diol resulting from the hydrolysis of 8,9 EET by sEH. The bars for the graphs are as stated for FIG. 2A. The graphs show that the combination of the COX-1 and -2 inhibitor indomethacin and with the sEHI AUDA-BE resulted in a greater decline in 8,9 DHET concentration compared to the concentrations when either agent was used alone.

Example 3

This Example sets forth materials and methods for tail flick and hind paw withdrawal studies showing response to pain stimuli.

Briefly, mice are kept under 12:12 h light: dark cycle and water and food is supplied ad libitum. Mice are trained for three days to the experimental chambers in 30 min sessions each time. The next day baseline readings are taken. Vehicle control (oleic oil) is then injected sc in the next day and measurements are taken. Two days later, animals are injected through the sc route with test compounds dissolved in the oil vehicle and their responses are recorded after 90 minutes.

Tail flick and hind paw withdrawal latency tests are conducted according to D'Amour and Smith, J Pharmacol Exp Ther 72:74-9 (1941), and Woolfe and McDonald, J Pharmacol Exp Ther, 80:300-7 (1944). In tail flick assays, mice are placed in restrainers and left undisturbed for 30 minutes. Readings are then taken by placing the posterior end of the tail onto a tail flick apparatus that has a radiant heat source set to 55 C. Five measurements per animal are taken at two-minute intervals. The latency to move the tail is recorded. In hind paw withdrawal assays, the mice are placed in an experimental chamber with a glass surface. The temperature of this surface is kept constant at 30° C. After a 30-minute period of acclimation, radiant heat is applied to the plantar surface of the hind paw. Five measurements per animal are taken at two-minute intervals. The latency to move the paw is recorded. Single factor Anova and t-test analysis are run on the data.

Example 4

This Example sets forth the results of studies testing the properties of sEHI as analgesics.

The t-test analysis suggests that both AUDA-butyl ester (P=0.032) and compound 950 (P=0.029) treatments produce a slight but significant analgesic effect in tail flick assay. However in the hind paw withdrawal assay, we find highly significant differences between groups for both inhibitors by ANOVA analysis (p-value=0.000128). Compound 950 even continues to have significant analgesic effect 4 hours after treatment. It is important to note that these assays are run without the induction of pain in the animals. Therefore, these assays measured inherent analgesic effects of these compounds.

Example 5

This Example reports the results of studies on the levels of various metabolites in animals administered an inflammatory agent, with or without a COX inhibitor and with or without an sEHI. In this and the other Examples below reporting studies on various metabolites, the effects of the inhibitors were determined on 65 metabolites by liquid chromatography-mass spectrometry on a tandem quad mass spectrometer. From these 65, metabolites relevant to the particular study are reported in the Examples. In some of the studies, the metabolites reported are specific COX metabolites, including two, 6-keto-PGF$_{1a}$ and TXB$_2$, considered to be associated with a higher risk for heart attack or stroke. In other studies, the metabolites were chosen because they show the effects of the inhibitors on metabolites from several pathways.

Figure 3:
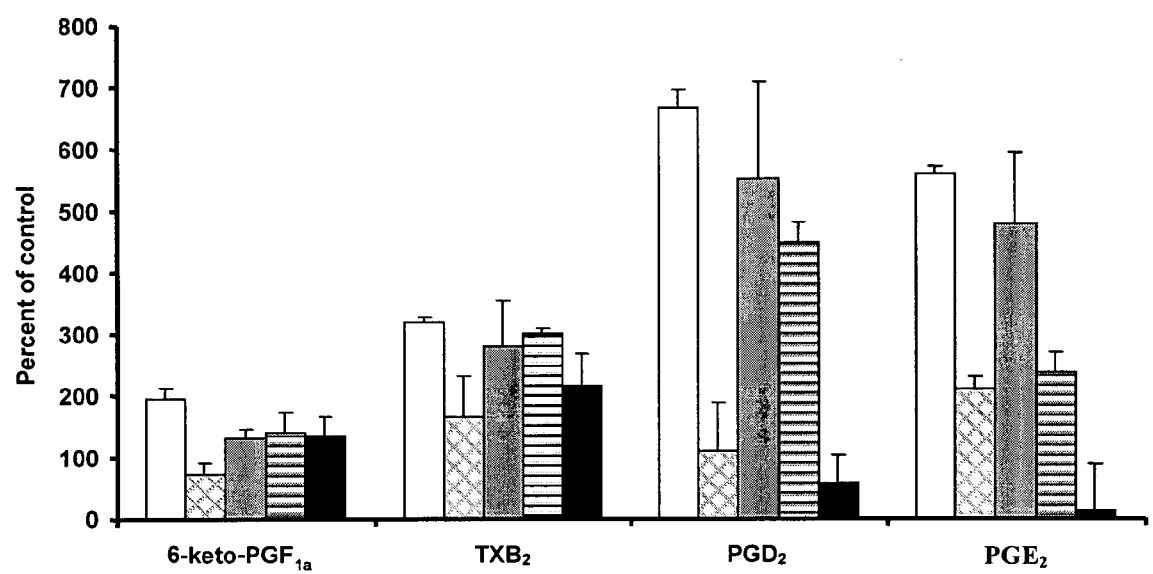
FIG. 3 shows the effect on four COX metabolites of administering the COX 2 inhibitor Celebrex® with or without the sEH inhibitor 12-(3-adamantane-1-yl-ureido)-dodecanoic acid-butyl ester ("AUDA-BE"). Horizontal axis: data for COX metabolites 6-keto-PGF$_{1\alpha}$, TXB2, PGD2, and PGE2. Vertical axis: depicts percentage of metabolite in test animals receiving designated treatment compared to that of control mice receiving vehicle without lipopolysaccharide ("LPS"). Data represent the average±SD (n=3) mouse plasma concentration after exposure to LPS (10 mg/Kg i.p.) White bars: LPS+vehicle, Crosshatch bars: LPS+Celebrex® (100 mg/Kg), Grey bars: LPS+Celebrex® (25 mg/Kg); Striped bars: AUDA-BE (20 mg/Kg) and Black bars: LPS+Celebrex® (25 mg/Kg)+AUDA-BE (20 mg/Kg).

FIG. 3 shows the effect on four COX metabolites of administering to mice lipopolysaccharide ("LPS"), with or without the exemplar COX-2 inhibitor Celebrex® and with or without an exemplar sEHI inhibitor, AUDA-BE.

The data indicate that using a prophylactic dose of AUDA-BE (20 mg/Kg, or "mpk") with a non-therapeutic dose of Celebrex® (25 mg/Kg) reduces the proinflammatory metabolites PGE$_2$ and PGD$_2$, while not affecting the levels of the metabolites 6-keto-PGF1a and TXB$_2$. 6-keto-PGF$_{1a}$ and TXB$_2$ are the stable metabolites of PGI$_2$ and TXA$_2$, which have been implicated in increased risk for stroke and heart attack. The combination therapy indicates a greater reduction in PGE$_2$ and PGD$_2$ than when using a therapeutic dose of Celebrex® (100 mg/Kg).

The study reported in FIG. 3 was repeated with a second exemplar sEH inhibitor, a polyether compound known as compound 950, with similar results.

Example 6

This Example reports the results of studies on the effect on five metabolites of administering to mice lipopolysaccharide ("LPS"), with or without the exemplar COX-1/2 inhibitor Indomethacin, with or without an exemplar sEHI inhibitor, AUDA-BE.

The metabolites chosen for study show the effect on different pathways by which arachidonic acid is metabolized. ΣEpOMEs and ΣDHOMEs are indicators of the P450 pathway, 5-HETE is an indicator of how much arachidonic acid is going through the 5-lipoxygenase pathway and 6-keto-PGF$_{1a}$, and PGE$_2$ are indicators of the arachidonic acid metabolized by the cyclooxygenase pathway.

Figure 4:
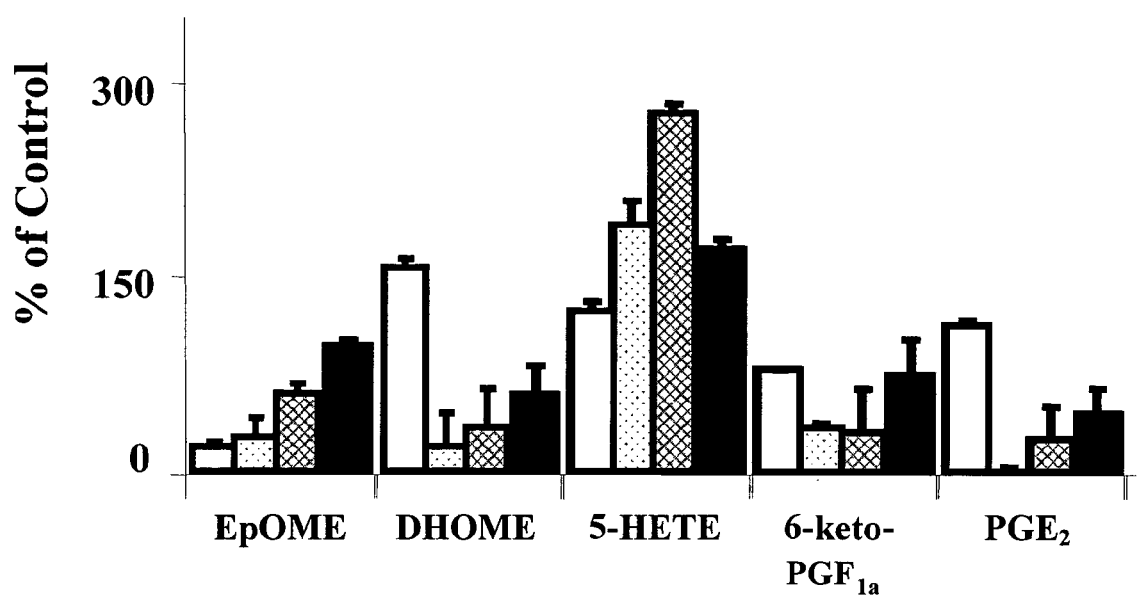
FIG. 4 shows the effect on five metabolites of administering the COX1/COX 2 inhibitor Indomethacin with or without the sEH inhibitor 12-(3-adamantane-1-yl-ureido)-dodecanoic acid butyl ester (AUDA-BE). Horizontal axis: data for metabolites EpOME, DHOME, 5-HETE, 6-keto-PGF$_{1\alpha}$, and PGE2. Vertical axis: depicts percentage of metabolite in test animals receiving designated treatment compared to that of control mice receiving vehicle without lipopolysaccharide ("LPS"). Data represent the average±SD (n=4) mouse plasma concentration after exposure to LPS (10 mg/Kg i.p.) White bars: LPS+vehicle, Dotted bars: saline+Indomethacin (100 mg/Kg, administered subcutaneously ("s.c." or "sc")), Crosshatched bars: LPS+Indomethacin (100 mg/Kg s.c.); Black bars: LPS+Indomethacin (50 mg/Kg s.c.)+AUDA-BE (20 mg/Kg s.c.).

The data shown in FIG. 4 indicate that using a prophylactic dose of AUDA-BE (20 mg/Kg, or "mpk") with a dose of Indomethacin (100 mg/Kg) reduces the proinflammatory metabolite PGE$_2$ without causing a dramatic increase in the proinflammatory 5-LOX (metabolite: 5-HETE) pathway. The effect of AUDA-BE (20 mg/Kg) on the same metabolites has also been determined. To maintain the legibility of the graphs, these results were not included in the Figure, but are summarized here: ΣEpOME=122±8%, ΣDHOME=141±15%, 5-HETE=262±21%; 6-keto-PGF$_{1a}$=128±6%, and PGE$_2$=241±2%.

Example 7

This Example reports the effect on four COX metabolites of administering to mice lipopolysaccharide ("LPS"), with or without the exemplar COX-2 inhibitor Vioxx®, with or without an exemplar sEHI inhibitor, AUDA-BE.

Figure 5:
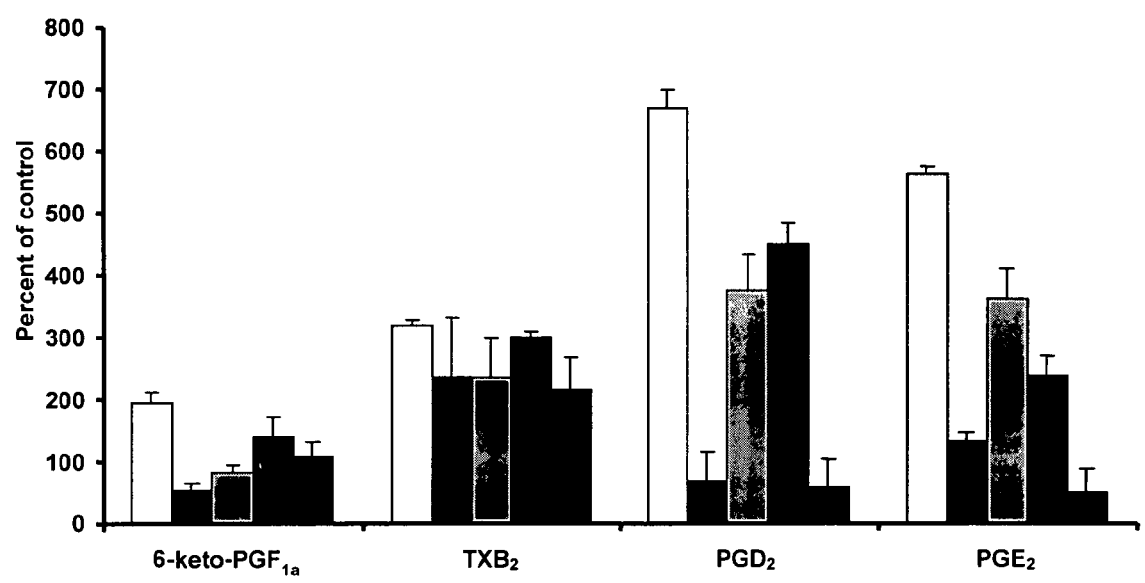
FIG. 5 shows the effect on four COX metabolites of administering the COX 2 inhibitor Vioxx® with or without the sEH inhibitor AUDA-BE. Horizontal axis: data for COX metabolites 6-keto-PGF$_{1\alpha}$, TXB2, PGD2, and PGE2. Vertical axis: depicts percentage of metabolite in test animals receiving designated treatment compared to that of control mice receiving vehicle without lipopolysaccharide ("LPS"). Data represent the average±SD (n=4) mouse plasma concentration after exposure to LPS (10 mg/Kg i.p.) White bars: LPS+vehicle, Crosshatch bars: LPS+Vioxx® (25 mg/Kg administered subcutaneously ("s.c." or "sc")), Grey bars: LPS+Vioxx® (10 mg/Kg sc); Striped bars: AUDA-BE (20 mg/Kg sc), Black bars: LPS+Vioxx® (10 mg/Kg sc)+AUDA-BE (20 mg/Kg sc).

As shown in FIG. 5, the data indicate that using a prophylactic dose of AUDA-BE (20 mg/Kg) with a non-optimum therapeutic dose of Vioxx® (10 mg/Kg) reduces the proinflammatory metabolites PGE2 and PGD2, while not affecting the metabolites 6-keto-PGF$_{1a}$ and TXB$_2$. 6-keto-PGF$_{1a}$ and TXB$_2$ are the stable metabolites of PGI$_2$ and TXA$_2$, which have been implicated in increased risk for stroke and heart attack. The combination of inhibitors provides a greater reduction in PGE$_2$ and PGD$_2$ with the non-optimum therapeutic dose of COX-2 inhibitor than use of a more optimal therapeutic dose of Vioxx® (25 mg/Kg) by itself.

The study reported in FIG. 5 was repeated with a second exemplar sEH inhibitor, a polyether compound known as compound 950, with similar results.

Example 8

This Example reports the results of studies on pain tolerance in animals to which a COX inhibitor or an exemplary sEHI, or both, have been administered.

Figure 6:
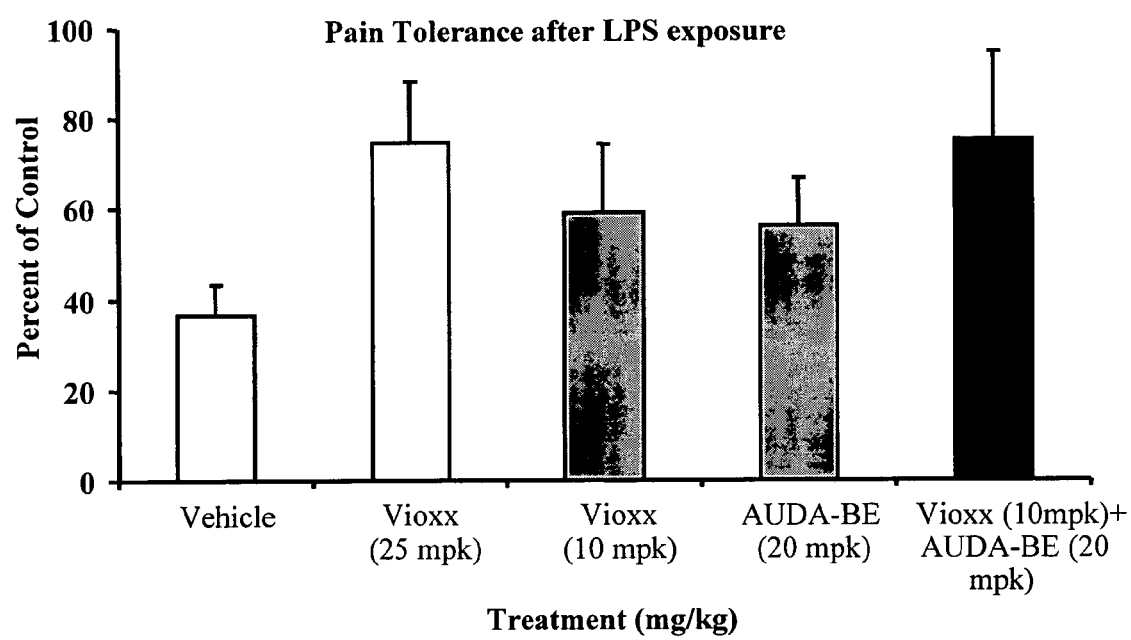
FIG. 6 shows the effect of various inhibitors or combinations of inhibitors on a hind paw withdrawal assay of animals prophylactically treated with the inhibitor(s) and then challenged with lipopolysaccharide ("LPS"). Horizontal axis: Treatments to change pain tollerance. Vertical axis: depicts percentage of pain tolerance in test animals receiving designated treatment and lipopolysaccharide ("LPS") compared to that of control mice receiving vehicle without LPS. Data represent the average±SD (n=4) time until a paw twitch is seen. LPS makes mice more sensitive to pain, while the data shows the inhibitors decrease the animal's response to a pain stimulus in the assay. White bar: control animal treated systemically with vehicle (oleic oil, administered subcutaneously ("s.c." or "sc")). Crosshatched bar: animal treated with Vioxx® at 25 mg/Kg sc. Gray bar: animal treated with Vioxx® at 10 mg/Kg sc. Striped bar: animal treated with AUDA-BE at 25 mg/Kg sc. Black bar: animal treated with Vioxx® at 10 mg/Kg sc and AUDA-BE at 20 mg/Kg sc.

FIG. 6 shows the effect on pain tolerance of mice administered lipopolysaccharide ("LPS") in oleic oil (the vehicle), LPS and a sub-optimal dosage of the COX-2 inhibitor Vioxx®, LPS and a therapeutic dosage of Vioxx®, LPS and with an exemplar sEHI inhibitor, AUDA-BE, or a combination of LPS and both the sub-optimal dosage of Vioxx® and AUDA-BE.

The dosages used in FIGS. 5 and 6 are the same. The data shown in FIG. 6 indicate that using a prophylactic dose of AUDA-BE (20 mg/Kg) with a sub-optimum therapeutic dose of Vioxx® (10 mg/Kg) increased the tolerance to pain. The combination of the two types of inhibitor increased tolerance to pain equal to that of a therapeutic dose of Vioxx® (25 mpk).

The study reported in FIG. 6 was repeated with indomethacin, which showed similar results, but with a different time course apparently due to the shorter half life of indomethacin compared to Vioxx®.

Example 9

Figure 7:
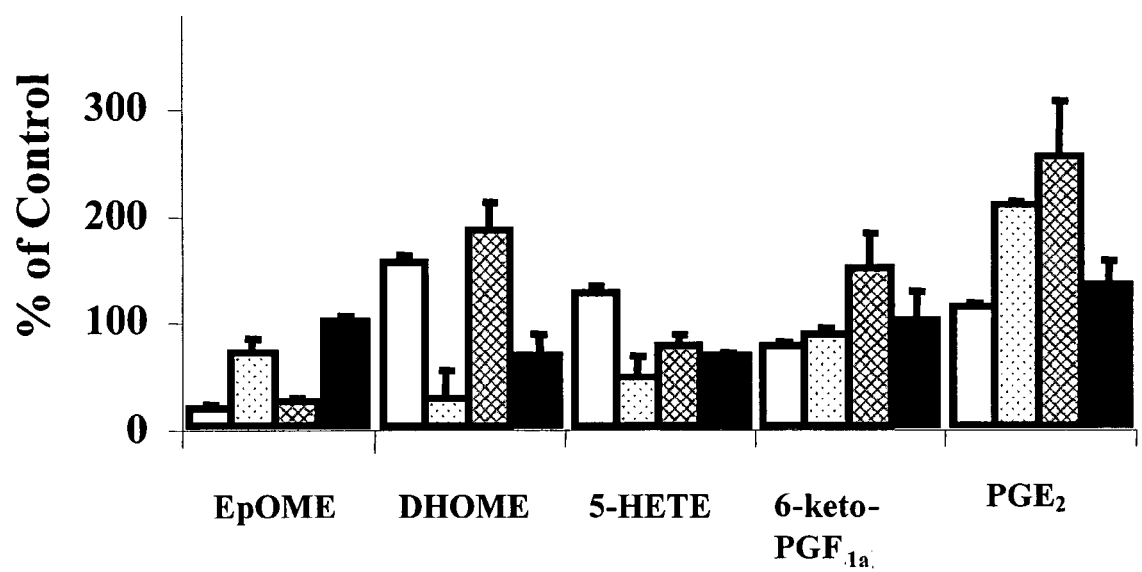
FIG. 7 shows the effect on five metabolites of administering the FLAP inhibitor MK886 with or without the sEH inhibitor AUDA-BE. Horizontal axis: data for metabolites EpOME, DHOME, 5-HETE, 6-keto-PGF$_{1\alpha}$, and PGE2. Vertical axis: depicts percentage of metabolite in test animals receiving designated treatment compared to that of control mice receiving vehicle without lipopolysaccharide ("LPS"). Data represent the average±SD (n=4) mouse plasma concentration after exposure to LPS (10 mg/Kg i.p.) White bars: LPS+vehicle, Dotted bars: saline+MK886 (50 mg/Kg administered subcutaneously ("s.c." or "sc")), Crosshatched bars: LPS+MK886 (50 mg/Kg sc); Black bars: LPS+MK886 (50 mg/Kg sc)+AUDA-BE (20 mg/Kg sc).

This Example reports the effect on five metabolites of administering to mice lipopolysaccharide ("LPS"), with or without the FLAP inhibitor MK886, and with or without an exemplar sEHI inhibitor, AUDA-BE. The results are shown in FIG. 7.

The data indicate that using a prophylactic dose of AUDA-BE (20 mg/Kg) with a dose of MK886 (50 mg/Kg) reduced the proinflammatory metabolite 5-HETE without causing a dramatic increase in the proinflammatory prostaglandin metabolites 6-keto-PGF$_{1a}$, and PGE$_2$. The effect of AUDA-BE (20 mg/Kg) on the same metabolites has also been determined. To maintain the legibility of the graphs, these results were not included in the Figure, but are summarized here: ΣEpOME=122±8%, ΣDHOME=141±15%, 5-HETE=262±21%; 6-keto-PGF$_{1a}$=128±6%, and PGE$_2$=241±2%.

Example 10

Western immunoblot analysis was performed with proteins isolated from liver to detect cycloxygenase 2 (COX-2). The isolated proteins were separated by electrophoresis on 10% SDS-PAGE and then transferred onto polyvinylidene fluoride membranes (Immobilon P, Millipore Corp., Bedford, Mass.). COX-2 protein was detected with polyclonal antibody from Cayman Chemical. The membranes were incubated with rabbit anti-mouse HRP-linked IgG (Amersham, Arlington Heights, Ill.) at 1:10,000 dilution, washed, then contacted with secondary antibody and visualized using SuperSignal® West Femto Maximum Sensitivity Substrate (Pierce Biotechnology, Inc., Rockford, Ill.), a chemiluminiscence detection system, per manufacturer's instructions. The immunodetectable bands were quantified by densitometry with Kodak 1.D Image Analysis System v. 3.5.4. (Kodak, Rochester, N.Y.).

Figure 8:
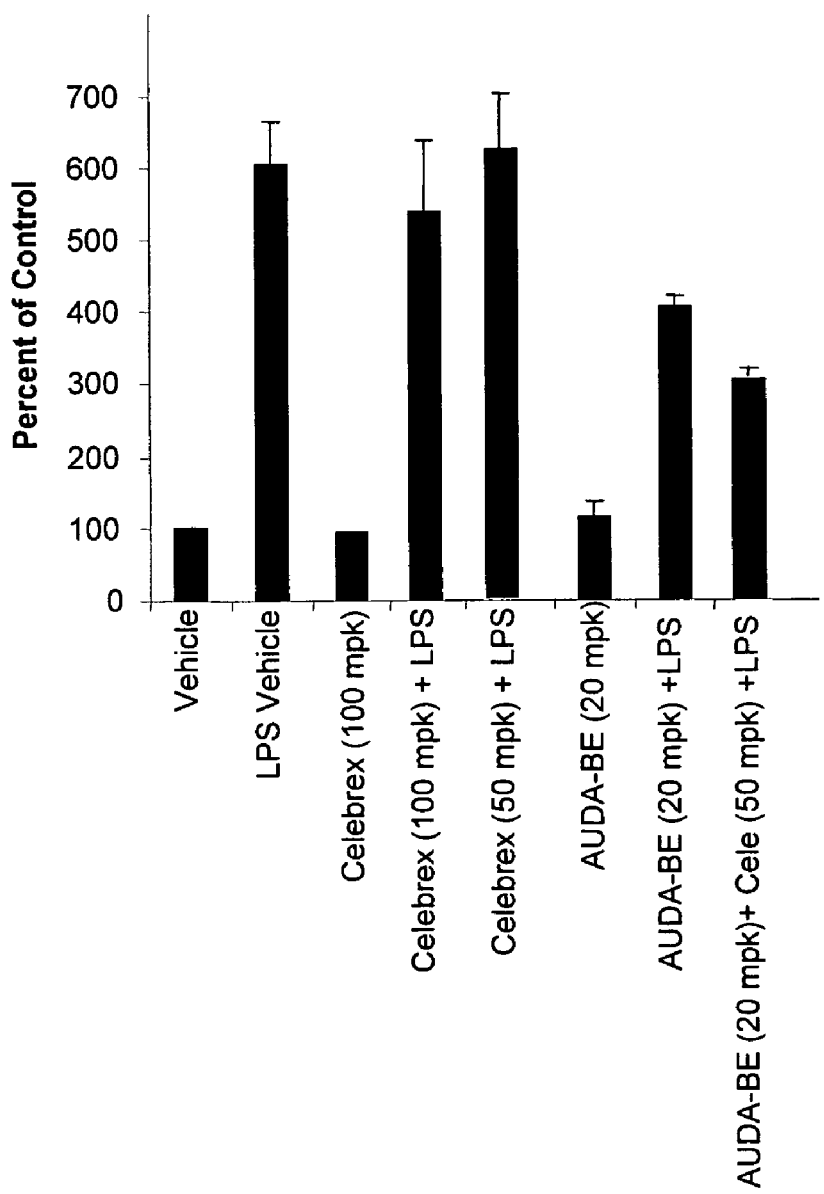
FIG. 8 shows the induction of COX2 protein in the livers of mice undergoing various treatments. Horizontal axis: treatment administered to the mice. First column: vehicle (oleic acid, administered subcutaneously ("s.c." or "sc")). Second column: lipopolysaccharide ("LPS", 10 mg/Kg i.p.) and vehicle. Third column: Celebrex® (100 mg/Kg sc). Fourth column: Celebrex® (100 mg/Kg sc)+LPS (10 mg/Kg i.p.). Fifth column: AUDA-BE (20 mg/Kg sc). Sixth column: AUDA-BE (20 mg/Kg sc)+LPS (10 mg/Kg i.p.). Seventh column: AUDA-BE (20 mg/Kg sc), Celebrex® (50 mg/Kg sc)+LPS (10 mg/Kg i.p.). Vertical axis: depicts percentage of protein induced in test animals receiving designated treatment compared to that of control mice receiving vehicle without LPS.

FIG. 8 shows the effect on COX-2 protein levels in the livers of mice exposed to vehicle only, to lipopolysaccharide ("LPS"), to an exemplar COX-2 inhibitor, to the COX-2 inhibitor+LPS, to an exemplar sEHI inhibitor, AUDA-BE, to the sEHI+LPS, or to the COX-2 inhibitor, the sEHI, and LPS. The error bars for the bars showing relating to the administration of vehicle alone and for the COX-2 inhibitor alone are too small to be depicted.

As shown in FIG. 8, mice administered 50 mg/Kg ("mpk") of the COX-2 inhibitor and LPS had approximately 6 times the amount of COX-2 as the control mice, roughly the same as mice administered LPS and vehicle alone, while mice administered the sEHI and LPS showed about 4 times the amount of COX-2 as control mice, a significant reduction. Further, mice administered LPS and both the COX-2 inhibitor and the sEHI had a lower level of COX-2 than mice administered LPS and either (a) COX-2 inhibitor or (b) the sEHI. This was a surprising result since administering LPS with the same amount (50 mg/Kg) of COX-2 inhibitor by itself did not reduce the amount of induced COX-2 below that induced by LPS administered without the COX-2 inhibitor.

The study reported in FIG. 8 was repeated with Vioxx®, with indomethacin, and with compound 950, with similar results.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for reducing undesirable side effects caused by administration of a cyclo-oxygenase (COX) inhibitor while maintaining efficacy of the COX inhibitor in reducing pain or inflammation in a subject in need thereof comprising co-administering (i) an inhibitor of soluble epoxide hydrolase (sEH) and (ii) a sub-therapeutic amount of the COX inhibitor, thereby reducing undesirable side effects caused by administration of the COX inhibitor while maintaining efficacy of the COX inhibitor in reducing pain or inflammation in the subject, wherein the COX inhibitor is a selective COX-2 inhibitor.

2. The method of claim 1, wherein the undesirable side effects are dose-dependent.

3. The method of claim 2, wherein the undesirable side effects are higher risk for heart attack and stroke.

4. The method of claim 2, wherein the undesirable side effects are gastrointestinal ulceration and bleeding.

5. The method of claim 2, wherein the undesirable side effects are inhibition of platelet aggregation and adverse changes in renal blood flow.

6. The method of claim 2, wherein the undesirable side effects are adverse changes in renal blood flow.

7. The method of claim 1, wherein the selective COX-2 inhibitor is selected from the group consisting of celecoxib, valdecoxib, lumiracoxib, etoricoxib and rofecoxib.

8. The method of claim 1, wherein the inhibitor of sEH has a primary pharmacophore selected from the group consisting of a urea, a carbamate and an amide.

9. The method of claim 1, wherein the inhibitor of sEH has a polyether secondary pharmacophore.

10. The method of claim 1, further comprising administering a cis-epoxyeicosantrienoic acid (EET) to said subject.

11. The method of claim 1, further comprising administering an epoxide of docosahexaenoic acid ("DHA") or of eicosapentaenoic acid ("EPA"), or an epoxide of DHA and an epoxide of EPA to said subject.

12. The method of claim 1, wherein the inhibitor of sEH and the COX-2 inhibitor are concurrently administered.

13. The method of claim 1, wherein the COX-2 inhibitor is administered within 4 hours of the inhibitor of sEH.

* * * * *